United States Patent
Istvan et al.

(10) Patent No.: US 7,197,357 B2
(45) Date of Patent: Mar. 27, 2007

(54) WIRELESS ECG SYSTEM

(75) Inventors: Rud Istvan, Fort Lauderdale, FL (US); Bill Gregory, Fort Lauderdale, FL (US); Kenneth Solovay, Weston, FL (US); David Paul Chastain, Acton, MA (US); John David Gundlach, Acton, MA (US); Nicholas C. Hopman, Lake Zurich, IL (US); Daniel L. Williams, Norwell, MA (US); Franco Lodato, Weston, FL (US); Michael Salem, Ft. Lauderdale, FL (US)

(73) Assignee: Life Sync Corporation, Fort Lauderdale, FL (US)

( * ) Notice: Subject to any disclaimer, the term of this patent is extended or adjusted under 35 U.S.C. 154(b) by 0 days.

(21) Appl. No.: 09/998,733

(22) Filed: Nov. 30, 2001

(65) Prior Publication Data

US 2003/0105403 A1 Jun. 5, 2003

Related U.S. Application Data

(63) Continuation-in-part of application No. 09/908,509, filed on Jul. 17, 2001, now Pat. No. 6,611,705.

(51) Int. Cl.
*A61B 5/04* (2006.01)

(52) U.S. Cl. ........................................ 600/509
(58) Field of Classification Search ............ 600/509, 600/512, 301, 372, 382, 386–391, 393, 523; 128/903
See application file for complete search history.

(56) References Cited

U.S. PATENT DOCUMENTS 2,958,781 A  11/1960  Marchal et al.
3,199,508 A  8/1965  Roth
3,495,584 A  2/1970  Schwalm (Continued)

FOREIGN PATENT DOCUMENTS

| DE | 1805444 | 5/1970 |
| DE | 2535858 | 2/1976 |
| DE | 3732714 | 4/1989 |

(Continued)

OTHER PUBLICATIONS

Kimmich, H,.P., "Clinical Telemetry and Patient Monitoring", Biotelemetry II: Proceedings of the Second International Symposium on Biotelemetry, 1974, pp. 190–195, Switzerland.

Zerzawy, R., "Simultaneous Wireless Telemetry for Several Biologic Measurements. Technics and Application of a New 4-Channel Telemetry", periodical—Z Kreislaufforsch, Feb. 1971, pp 162–169, vol. 60 part 2.

Retzke, F., "Experience with a Mobile Monitoring System for Fetal and Neonatal Cardiotachometry", periodical—Zentralbl Gynakol, 1984, pp 545–549, vol. 106.

Van Rijn, A.C.M., "Modelling of Biopotential Recordings and It's Implications for Instrumentation Design", doctoral thesis—available from the National Technical Information Service, Springfield, VA., Nov. 8, 1993, 153 pages.

(Continued)

*Primary Examiner*—George Manuel
*Assistant Examiner*—Dana D. Greene
(74) *Attorney, Agent, or Firm*—Lott & Friedland, P.A.

(57) ABSTRACT

A cardiac monitoring system and, more particularly, a wireless electrocardiograph (ECG) system. The present invention detects electrical signals from a patient's heart and transmits the signals digitally to a remote base station via telemetry. The base station converts the digital signals back to an analog electrical signals that can be read by an ECG monitor.

25 Claims, 13 Drawing Sheets

U.S. PATENT DOCUMENTS

| | | | |
|---|---|---|---|
| 3,602,215 A | 8/1971 | Parnell | |
| 3,603,881 A | 9/1971 | Thornton | |
| 3,727,190 A | 4/1973 | Vogelman | |
| 3,729,708 A | 4/1973 | Wolfer | |
| 3,757,778 A | 9/1973 | Graham | |
| 3,774,594 A | 11/1973 | Huszar | |
| 3,810,102 A | 5/1974 | Parks, III | |
| 3,830,228 A | 8/1974 | Foner | |
| 3,834,373 A | 9/1974 | Sato | |
| 3,905,364 A | 9/1975 | Cudahy | |
| 3,910,260 A | 10/1975 | Sarnoff | |
| 3,925,762 A | 12/1975 | Heitlinger | |
| 3,943,918 A * | 3/1976 | Lewis | 600/392 |
| 3,970,996 A | 7/1976 | Yasaka | |
| 3,986,498 A | 10/1976 | Lewis | |
| 4,027,663 A | 6/1977 | Fischler | |
| 4,042,906 A | 8/1977 | Ezell | |
| 4,051,522 A | 9/1977 | Healy | |
| 4,074,228 A | 2/1978 | Jonscher | |
| 4,121,573 A | 10/1978 | Crovella et al. | |
| 4,124,894 A | 11/1978 | Vick | |
| 4,141,351 A | 2/1979 | James et al. | |
| 4,150,284 A | 4/1979 | Trenkler et al. | |
| 4,156,867 A | 5/1979 | Bench | |
| 4,173,221 A | 11/1979 | McLaughlin | |
| 4,173,971 A | 11/1979 | Karz | |
| 4,186,749 A | 2/1980 | Fryer | |
| 4,216,462 A | 8/1980 | McGrath | |
| 4,233,241 A | 11/1980 | Kalopissis | |
| 4,237,900 A | 12/1980 | Schulman et al. | |
| 4,260,951 A | 4/1981 | Lewyn | |
| 4,262,632 A | 4/1981 | Hanton | |
| 4,281,664 A | 8/1981 | Duggan | |
| 4,321,933 A | 3/1982 | Baessler | |
| 4,328,814 A | 5/1982 | Arkans | |
| 4,353,372 A | 10/1982 | Ayer | |
| 4,396,906 A | 8/1983 | Weaver | |
| 4,425,921 A | 1/1984 | Fujisaki | |
| 4,441,498 A | 4/1984 | Nordling | |
| 4,449,536 A | 5/1984 | Weaver | |
| 4,471,786 A | 9/1984 | Inagaki et al. | |
| 4,475,208 A | 10/1984 | Ricketts | |
| 4,494,552 A | 1/1985 | Heath | |
| 4,510,495 A | 4/1985 | Sigrimis | |
| 4,521,918 A | 6/1985 | Challen | |
| 4,531,526 A | 7/1985 | Genest | |
| 4,539,995 A | 9/1985 | Segawa | |
| 4,556,061 A | 12/1985 | Barreras et al. | |
| 4,556,063 A | 12/1985 | Thompson et al. | |
| 4,562,840 A | 1/1986 | Batina et al. | |
| 4,573,026 A | 2/1986 | Curtis | |
| 4,583,548 A | 4/1986 | Schmid | |
| 4,583,549 A | 4/1986 | Manoli | |
| 4,585,004 A | 4/1986 | Brownlee | |
| 4,586,508 A | 5/1986 | Batina et al. | |
| 4,598,281 A | 7/1986 | Maas | |
| 4,599,723 A | 7/1986 | Eck | |
| 4,601,043 A | 7/1986 | Hardt | |
| 4,606,352 A | 8/1986 | Geddes | |
| 4,608,987 A | 9/1986 | Mills | |
| 4,618,861 A | 10/1986 | Gettens et al. | |
| 4,625,733 A | 12/1986 | Saynajakangas | |
| RE32,361 E | 2/1987 | Duggan | |
| 4,653,068 A | 3/1987 | Kadin | |
| 4,681,118 A | 7/1987 | Asai et al. | |
| 4,709,704 A | 12/1987 | Lukasiewicz | |
| 4,724,435 A | 2/1988 | Moses | |
| 4,747,413 A | 5/1988 | Bloch | |
| 4,754,483 A | 6/1988 | Weaver | |
| 4,783,844 A | 11/1988 | Higashiyama et al. | |
| 4,784,162 A | 11/1988 | Ricks et al. | |
| 4,791,933 A | 12/1988 | Asai et al. | |
| 4,794,532 A | 12/1988 | Leckband et al. | |
| 4,799,059 A | 1/1989 | Grindahl | |
| 4,802,222 A | 1/1989 | Weaver | |
| 4,803,625 A | 2/1989 | Fu et al. | |
| 4,805,631 A | 2/1989 | Roi du Maroc, II. | |
| 4,835,372 A | 5/1989 | Gombrich | |
| 4,839,806 A | 6/1989 | Goldfischer | |
| 4,850,009 A | 7/1989 | Zook | |
| 4,852,572 A | 8/1989 | Nakahashi et al. | |
| 4,860,759 A | 8/1989 | Kahn et al. | |
| 4,865,044 A | 9/1989 | Wallace | |
| 4,883,064 A | 11/1989 | Olson | |
| 4,889,131 A | 12/1989 | Salem et al. | |
| 4,889,132 A | 12/1989 | Hutcheson | |
| 4,909,260 A | 3/1990 | Salem et al. | |
| 4,916,441 A | 4/1990 | Gombrich | |
| 4,928,187 A | 5/1990 | Rees | |
| 4,955,075 A | 9/1990 | Anderson | |
| 4,957,109 A | 9/1990 | Groeger et al. | |
| 4,958,645 A | 9/1990 | Cadell et al. | |
| 4,966,154 A | 10/1990 | Cooper et al. | |
| 4,974,607 A | 12/1990 | Miwa | |
| 4,981,141 A | 1/1991 | Segalowitz | |
| 5,012,411 A | 4/1991 | Policastro et al. | |
| 5,025,452 A | 6/1991 | Sohner | |
| 5,025,808 A | 6/1991 | Hafner | |
| 5,026,462 A | 6/1991 | Butterfield et al. | |
| 5,036,869 A | 8/1991 | Inahara | |
| 5,042,498 A | 8/1991 | Dukes | |
| 5,051,799 A | 9/1991 | Paul et al. | |
| 5,072,383 A | 12/1991 | Brimm | |
| 5,077,753 A | 12/1991 | Grau | |
| 5,078,134 A | 1/1992 | Heilman | |
| 5,085,224 A | 2/1992 | Galen | |
| 5,109,845 A | 5/1992 | Yuuchi et al. | |
| 5,113,869 A | 5/1992 | Nappholz et al. | |
| 5,127,404 A | 7/1992 | Wyborny | |
| 5,131,399 A | 7/1992 | Sciarra | |
| 5,137,022 A | 8/1992 | Henry | |
| 5,153,584 A | 10/1992 | Engira | |
| 5,157,604 A | 10/1992 | Axford | |
| 5,168,874 A | 12/1992 | Segalowitz | |
| 5,171,977 A | 12/1992 | Morrison | |
| 5,177,765 A | 1/1993 | Holland | |
| 5,177,766 A | 1/1993 | Holland | |
| 5,179,569 A | 1/1993 | Sawyer | |
| 5,179,571 A | 1/1993 | Schilling | |
| 5,181,519 A | 1/1993 | Bible | |
| 5,184,620 A | 2/1993 | Cudahy | |
| 5,191,886 A * | 3/1993 | Paeth et al. | 600/382 |
| 5,192,949 A | 3/1993 | Suzuki | |
| 5,205,294 A | 4/1993 | Flach et al. | |
| 5,212,476 A | 5/1993 | Maloney | |
| 5,212,715 A | 5/1993 | Pickert | |
| 5,224,479 A | 7/1993 | Sekine | |
| 5,224,485 A | 7/1993 | Powers | |
| 5,226,431 A | 7/1993 | Bible et al. | |
| 5,238,001 A | 8/1993 | Gallant et al. | |
| 5,270,811 A | 12/1993 | Ishibashi | |
| 5,272,477 A | 12/1993 | Tashima | |
| 5,292,343 A | 3/1994 | Blanchette | |
| 5,305,202 A | 4/1994 | Gallant | |
| 5,305,353 A | 4/1994 | Weerackody | |
| 5,307,372 A | 4/1994 | Sawyer | |
| 5,307,817 A | 5/1994 | Guggenbuhl | |
| 5,307,818 A * | 5/1994 | Segalowitz | 600/509 |
| 5,309,920 A | 5/1994 | Gallant et al. | |
| 5,314,450 A | 5/1994 | Thompson | |
| 5,319,363 A | 6/1994 | Welch et al. | |

| | | | | | | |
|---|---|---|---|---|---|---|
| 5,327,888 A | | 7/1994 | Imran | 5,759,199 A | 6/1998 | Snell et al. |
| 5,335,664 A | | 8/1994 | Nagashima | 5,767,791 A | 6/1998 | Stoop et al. |
| 5,339,824 A | * | 8/1994 | Engira ........................ 600/525 | 5,776,057 A | 7/1998 | Swenson |
| 5,341,806 A | | 8/1994 | Gadsby et al. | 5,779,630 A | 7/1998 | Fein |
| 5,342,408 A | | 8/1994 | deCoriolis | 5,782,238 A | 7/1998 | Beitler |
| 5,343,869 A | | 9/1994 | Pross | 5,788,633 A | 8/1998 | Mahoney |
| 5,343,870 A | | 9/1994 | Gallant et al. | 5,800,204 A | 9/1998 | Nitsu |
| 5,348,008 A | | 9/1994 | Bornn et al. | 5,813,404 A | 9/1998 | Devlin |
| 5,353,791 A | | 10/1994 | Tamura | 5,819,740 A | 10/1998 | Muhlenberg |
| 5,353,793 A | | 10/1994 | Bornn | 5,820,567 A | 10/1998 | Mackie |
| 5,354,319 A | | 10/1994 | Wyborny | 5,827,179 A | 10/1998 | Lichter |
| 5,359,641 A | | 10/1994 | Schull | 5,855,550 A | 1/1999 | Lai |
| 5,365,530 A | | 11/1994 | Yoshida | 5,862,803 A | 1/1999 | Besson et al. |
| 5,375,604 A | | 12/1994 | Kelly et al. | 5,865,733 A | 2/1999 | Malinouskas et al. |
| 5,377,222 A | | 12/1994 | Sanderford, Jr. | 5,865,741 A | 2/1999 | Kelly et al. |
| 5,381,798 A | | 1/1995 | Burrows | 5,868,671 A | 2/1999 | Mahoney |
| 5,392,771 A | | 2/1995 | Mock | 5,871,451 A | 2/1999 | Unger et al. |
| 5,394,882 A | | 3/1995 | Mawhinney | 5,873,369 A | 2/1999 | Laniado |
| 5,400,794 A | | 3/1995 | Gorman | 5,873,821 A | 2/1999 | Chance et al. |
| 5,417,222 A | | 5/1995 | Dempsey | 5,882,300 A | 3/1999 | Malinouskas et al. |
| 5,438,607 A | | 8/1995 | Pzygoda | 5,899,928 A | 5/1999 | Sholder et al. |
| 5,441,047 A | | 8/1995 | David et al. | 5,899,931 A | 5/1999 | Deschamp et al. |
| 5,444,719 A | | 8/1995 | Cox et al. | 5,907,291 A | 5/1999 | Chen et al. |
| 5,458,122 A | | 10/1995 | Hethuin | 5,913,827 A | 6/1999 | Gorman |
| 5,458,123 A | | 10/1995 | Unger | 5,916,159 A | 6/1999 | Kelly et al. |
| 5,458,124 A | | 10/1995 | Stanko et al. | 5,917,414 A | 6/1999 | Oppelt |
| 5,464,021 A | | 11/1995 | Birnbaum | 5,919,141 A | 7/1999 | Money et al. |
| 5,485,848 A | | 1/1996 | Jackson et al. | 5,919,214 A | 7/1999 | Ciciarelli et al. |
| 5,491,474 A | | 2/1996 | Suni et al. | 5,931,791 A | 8/1999 | Saltzstein |
| 5,507,035 A | | 4/1996 | Bantz | 5,935,078 A | 8/1999 | Feierbach |
| 5,511,553 A | | 4/1996 | Segalowitz | 5,938,597 A | 8/1999 | Stratbucker |
| 5,522,396 A | | 6/1996 | Langer et al. | 5,944,659 A | 8/1999 | Flach et al. |
| 5,524,637 A | | 6/1996 | Erickson | 5,949,352 A | 9/1999 | Ferrari |
| 5,538,007 A | | 7/1996 | Gorman | 5,954,536 A | 9/1999 | Fuerst et al. |
| 5,544,649 A | | 8/1996 | David et al. | 5,954,719 A | 9/1999 | Chen et al. |
| 5,544,661 A | | 8/1996 | Davis et al. | 5,957,854 A | 9/1999 | Besson et al. |
| 5,546,950 A | | 8/1996 | Schoeckert et al. | 5,959,529 A | 9/1999 | Kail, IV |
| 5,549,113 A | | 8/1996 | Halleck et al. | 5,961,448 A | 10/1999 | Swenson |
| 5,564,429 A | | 10/1996 | Bornn | 5,963,650 A | 10/1999 | Simionescu et al. |
| 5,568,814 A | | 10/1996 | Gallant et al. | 5,964,701 A | 10/1999 | Asada et al. |
| 5,575,284 A | | 11/1996 | Athan et al. | 5,970,105 A | 10/1999 | Dacus |
| 5,576,952 A | | 11/1996 | Stutman | 5,999,857 A | 12/1999 | Weijand et al. |
| 5,579,001 A | | 11/1996 | Dempsey | 6,009,350 A | 12/1999 | Renken |
| 5,579,378 A | | 11/1996 | Arlinghaus | 6,010,359 A | 1/2000 | Etters et al. |
| 5,579,775 A | | 12/1996 | Iempsey | 6,027,363 A | 2/2000 | Watt et al. |
| 5,579,781 A | | 12/1996 | Cooke | 6,039,600 A | 3/2000 | Etters et al. |
| 5,582,180 A | | 12/1996 | Manset | 6,047,201 A | 4/2000 | Jackson, III |
| 5,586,552 A | | 12/1996 | Sakai | 6,053,887 A | 4/2000 | Levitas |
| 5,617,871 A | | 4/1997 | Burrows | 6,055,448 A | 4/2000 | Anderson et al. |
| 5,623,925 A | | 4/1997 | Swenson | 6,057,758 A | 5/2000 | Dempsey et al. |
| 5,628,324 A | | 5/1997 | Sarbach | 6,066,093 A | 5/2000 | Kelly |
| 5,628,326 A | | 5/1997 | Arand et al. | 6,074,345 A | 6/2000 | van Oostrom et al. |
| 5,634,468 A | | 6/1997 | Platt et al. | 6,076,003 A | * 6/2000 | Rogel ........................ 600/390 |
| 5,640,953 A | | 6/1997 | Bishop | 6,077,124 A | 6/2000 | Etters et al. |
| 5,645,059 A | | 7/1997 | Fein et al. | 6,083,248 A | 7/2000 | Thompson |
| 5,645,571 A | * | 7/1997 | Olson et al. .................... 607/5 | 6,086,412 A | 7/2000 | Watt et al. |
| 5,646,701 A | | 7/1997 | Duckworth | 6,093,146 A | 7/2000 | Filangeri |
| 5,664,270 A | | 9/1997 | Bell | 6,102,856 A | 8/2000 | Groff et al. |
| 5,669,391 A | | 9/1997 | Williams | 6,115,622 A | * 9/2000 | Minoz ........................ 600/361 |
| 5,678,545 A | | 10/1997 | Stratbucker | 6,117,076 A | 9/2000 | Cassidy |
| 5,678,562 A | | 10/1997 | Sellers | 6,119,029 A | * 9/2000 | Williams .................... 600/361 |
| 5,685,303 A | | 11/1997 | Rollman | 6,139,495 A | * 10/2000 | De La Huerga ............ 600/300 |
| 5,690,119 A | | 11/1997 | Rytky et al. | 6,141,575 A | 10/2000 | Price |
| 5,694,940 A | | 12/1997 | Unger et al. | 6,146,190 A | 11/2000 | Fuerst et al. |
| 5,704,351 A | | 1/1998 | Mortara et al. | 6,147,618 A | 11/2000 | Halleck |
| 5,718,234 A | | 2/1998 | Warden et al. | 6,149,602 A | 11/2000 | Arcelus |
| 5,720,771 A | | 2/1998 | Snell | 6,150,951 A | * 11/2000 | Olejniczak .................. 340/2.8 |
| 5,738,102 A | | 4/1998 | Lemelson | 6,154,676 A | 11/2000 | Levine |
| 5,746,207 A | * | 5/1998 | McLaughlin et al. ........ 600/372 | 6,157,851 A | 12/2000 | Kelly et al. |
| 5,748,103 A | | 5/1998 | Flach et al. | 6,198,394 B1 | 3/2001 | Jacobsen |
| 5,755,230 A | | 5/1998 | Schmidt et al. | 6,206,837 B1 | 3/2001 | Brugnoli |

| | | |
|---|---|---|
| 6,213,942 B1 | 4/2001 | Flach et al. |
| 6,219,568 B1 | 4/2001 | Kelly et al. |
| 6,219,569 B1 | 4/2001 | Kelly et al. |
| 6,225,901 B1 | 5/2001 | Kail |
| 6,236,874 B1 | 5/2001 | Devlin |
| 6,238,338 B1 | 5/2001 | DeLuca et al. |
| 6,244,890 B1 | 6/2001 | Fuerst et al. |
| 6,259,939 B1 * | 7/2001 | Rogel .................. 600/390 |
| 6,267,723 B1 | 7/2001 | Matsumura |
| 6,287,252 B1 | 9/2001 | Lugo |
| 6,289,238 B1 | 9/2001 | Besson |
| 6,295,466 B1 | 9/2001 | Ishikawa et al. |
| 6,304,774 B1 | 10/2001 | Gorman |
| 6,319,200 B1 | 11/2001 | Lai |
| 6,332,094 B1 | 12/2001 | Gorman |
| 6,364,834 B1 | 4/2002 | Reuss |
| 6,389,308 B1 | 5/2002 | Shusterman |
| 6,408,200 B1 | 6/2002 | Takashina |
| 6,415,169 B1 | 7/2002 | Kornrumpf et al. |
| 6,416,471 B1 | 7/2002 | Kumar |
| 6,440,067 B1 | 8/2002 | DeLuca |
| 6,441,747 B1 | 8/2002 | Khair |
| 6,443,890 B1 | 9/2002 | Schulze et al. |
| 6,450,953 B1 | 9/2002 | Place |
| 6,453,186 B1 | 9/2002 | Lovejoy et al. |
| 6,454,708 B1 | 9/2002 | Ferguson et al. |
| 6,470,893 B1 | 10/2002 | Boesen |
| 6,480,733 B1 | 11/2002 | Turcott |
| 6,496,705 B1 | 12/2002 | Ng |
| 6,544,173 B2 | 4/2003 | West et al. |
| 6,544,174 B2 | 4/2003 | West et al. |
| 6,560,473 B2 | 5/2003 | Dominguez |
| 6,602,191 B2 | 8/2003 | Quy |
| 6,616,606 B1 | 9/2003 | Petersen et al. |
| 6,654,631 B1 | 11/2003 | Sahai |
| 6,694,180 B1 | 2/2004 | Boesen |

FOREIGN PATENT DOCUMENTS

| | | |
|---|---|---|
| DE | 4034019 | 7/1992 |
| EP | 0212278 | 3/1987 |
| EP | 0354251 | 2/1990 |
| EP | 0719108 | 7/1996 |
| EP | 880 936 A2 | 12/1998 |
| FR | 0 048 187 A1 | 7/1981 |
| JP | 5-329121 | 6/1992 |
| JP | 5-220119 | 8/1993 |
| JP | 5-298589 | 11/1993 |
| JP | 5-329120 | 12/1993 |
| JP | H05 334458 | 12/1993 |
| JP | H09-19409 | 1/1997 |
| WO | WO 87/06113 | 10/1987 |
| WO | WO 90/08501 | 9/1990 |
| WO | WO9401039 | 1/1994 |
| WO | WO 95/07048 | 3/1995 |
| WO | WO9516388 | 6/1995 |
| WO | WO 97/49077 | 12/1997 |
| WO | WO 00/62663 | 10/2000 |
| WO | WO 00/62664 | 10/2000 |
| WO | WO 00/62665 | 10/2000 |
| WO | WO0062667 | 10/2000 |
| WO | WO 00/62667 | 10/2000 |
| WO | WO 01/89362 | 11/2001 |

OTHER PUBLICATIONS

Niitani, H., "Telemetry with Special Reference to Wireless Transmission of Electrocardiogram", periodical—Nippon Rinsho, Dec. 1969, pp 2873–2882, vol. 27 part 12.

Kimmich, H.P., "Biotelemetry in Anesthesia and Intensive Care", periodical—Anesth Analg (Paris), 1979, pp 383–387, vol. 36 part 9–10.

Henne, B., "Comparison Between Wilson's Thoracic Leads and the Telemetrically Transmitted Lead CM6 in Patients with Heart Diseases During Exertion", periodical—Z Kardiol, Mar. 1975, pp 274–280, vol. 64 part 3.

Baumgarten, K., "Wireless Transmission of the Fetal Electrocardiogram and Fetal Heart Beat During Pregnancy and Labor", periodical—Arch Gynakol, 1967, pp 267–268, vol. 204 part 2.

Muller, S., "Multifrequency Selective RF Pulses for Multi-slice MR Imaging", periodical—Magnetic Resonancy in Medicine, 1988, pp 364–372, vol. 6 part 3.

Harlow, H.J., "Adrenal Responsiveness in Domestic Sheep (Ovis aries) to Acute and Chronic Stressors as Predicted by Remote Monitoring of Cardiac Frequency", periodical—Canadian Journal of Zoology, 1987, pp 2021–2027, vol. 65 part 8.

Spraggins, T.A., "Wireless Retrospective Gating: Application to Cine Cardiac Imaging", periodical—Magnetic Resonance Imaging, 1990, pp 675–681, vol. 8 part 6.

White, R.D., "Electrocardiograph—Independent, "Wireless" Cardiovascular Cine MR Imaging", periodical—Magnetic Resonance Imaging, May–Jun. 1991, pp 347–355, vol. 1 part 3.

Watkinson, W.P., "Improved technique for Monitoring Electrocardiograms During Exposure to Radio–Frequency Radiation", periodical—AM J Physiological Society, 1986, pp H320–324, vol. 250 part 2.

Annovazzi–Lodi, Valerio, "Optoelectronic Telemetry of Electrophysiological Signals", periodical—Proceedings of SPIE, 1990, pp 113–119, vol. 1355.

Schulze, H.J., "The Telemetric Emergency Electrocardiography—Practical Use and Methodologic Effectiveness", periodical—Z Gesamete Inn Med, Dec. 15, 1986, pp 685–689, vol. 41 part 24.

Jones, J.W., "Remote Monitoring of Free Flaps with Telephonic Transmission of Photoplethysmograph Waveforms", periodical—Journal of Reconstructive Microsurgery, Apr. 1989, pp 141–144, vol. 5 part 2.

Bashein, G., "Anesthesia and Remote Monitoring for Intra-operative Radiation Therapy", periodical—Anesthesiology, Jun. 1986, pp 804–807, vol. 64 part 6.

Athan, Stephan, "Benefits of Spread Spectrum Technology in Present and Future Health Care Applications", conference—15th Annual International Conference IEEE Eng in Med & bio Soc, San Diego, CA, 1993, pp 1045–1046, vol. 15 part 2.

Hanley, J., "Telemetry in Health Care", periodical—Biomedical Engineering, Aug. 1976, pp 269–272, vol. 11 part 8.

* cited by examiner

FIG. 7
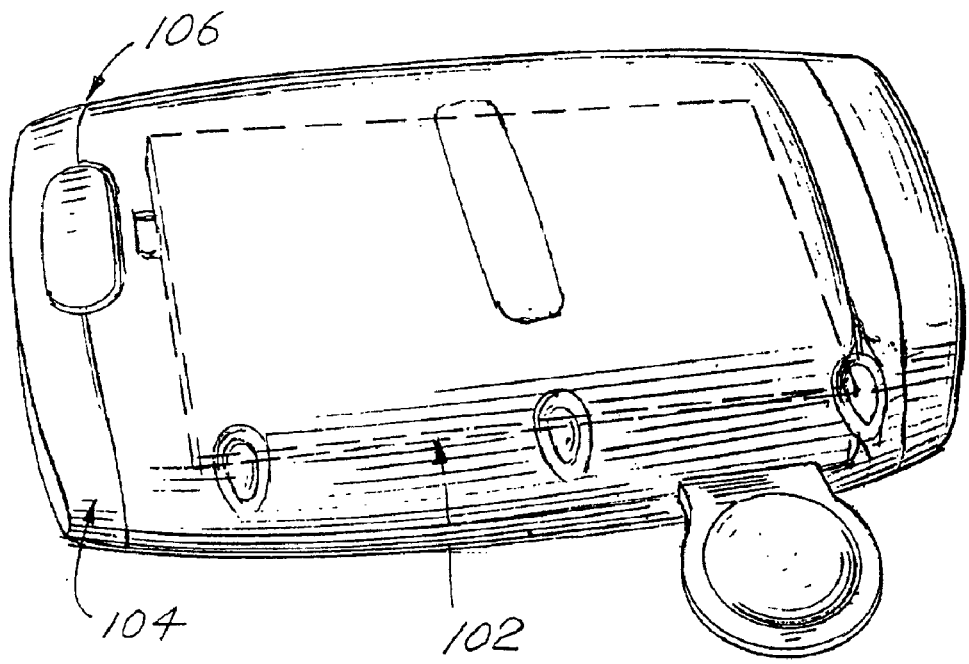
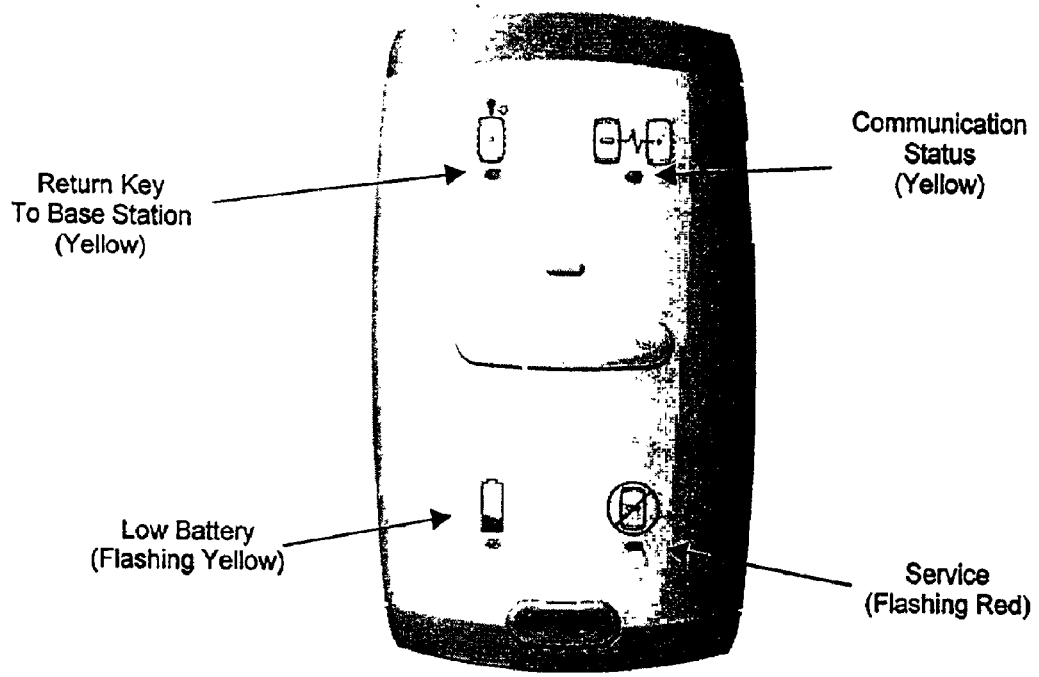
FIG. 7A

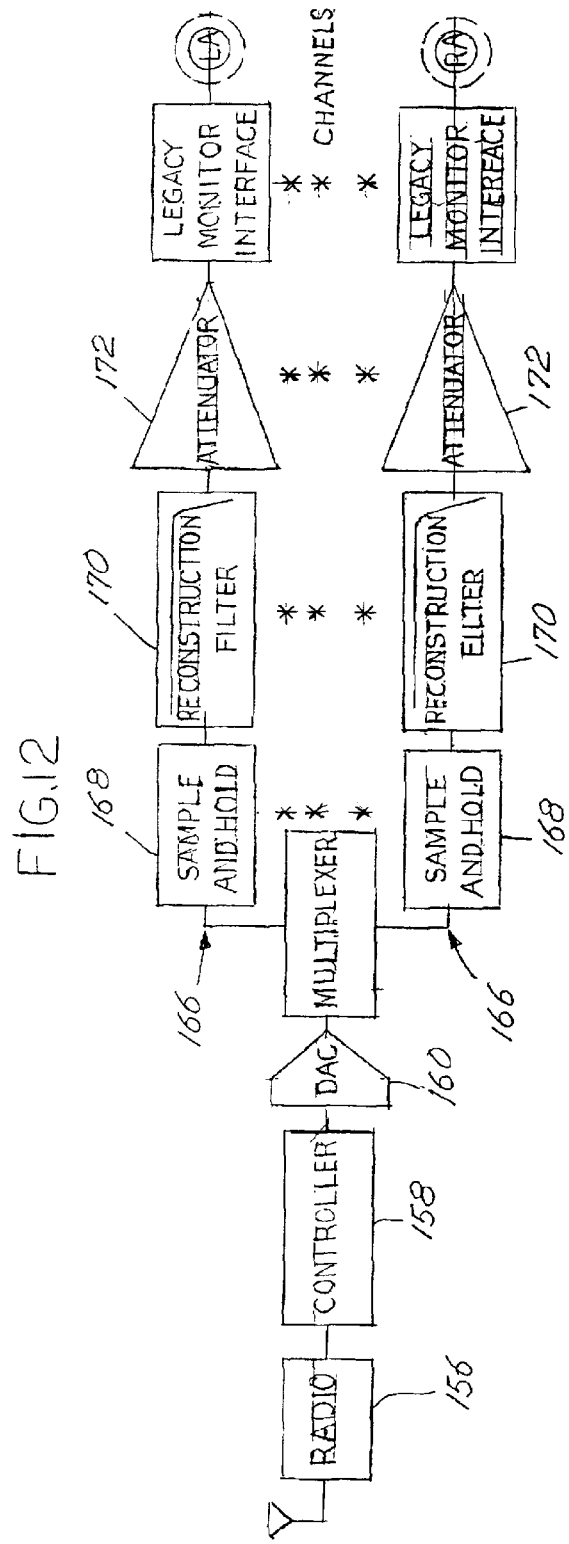

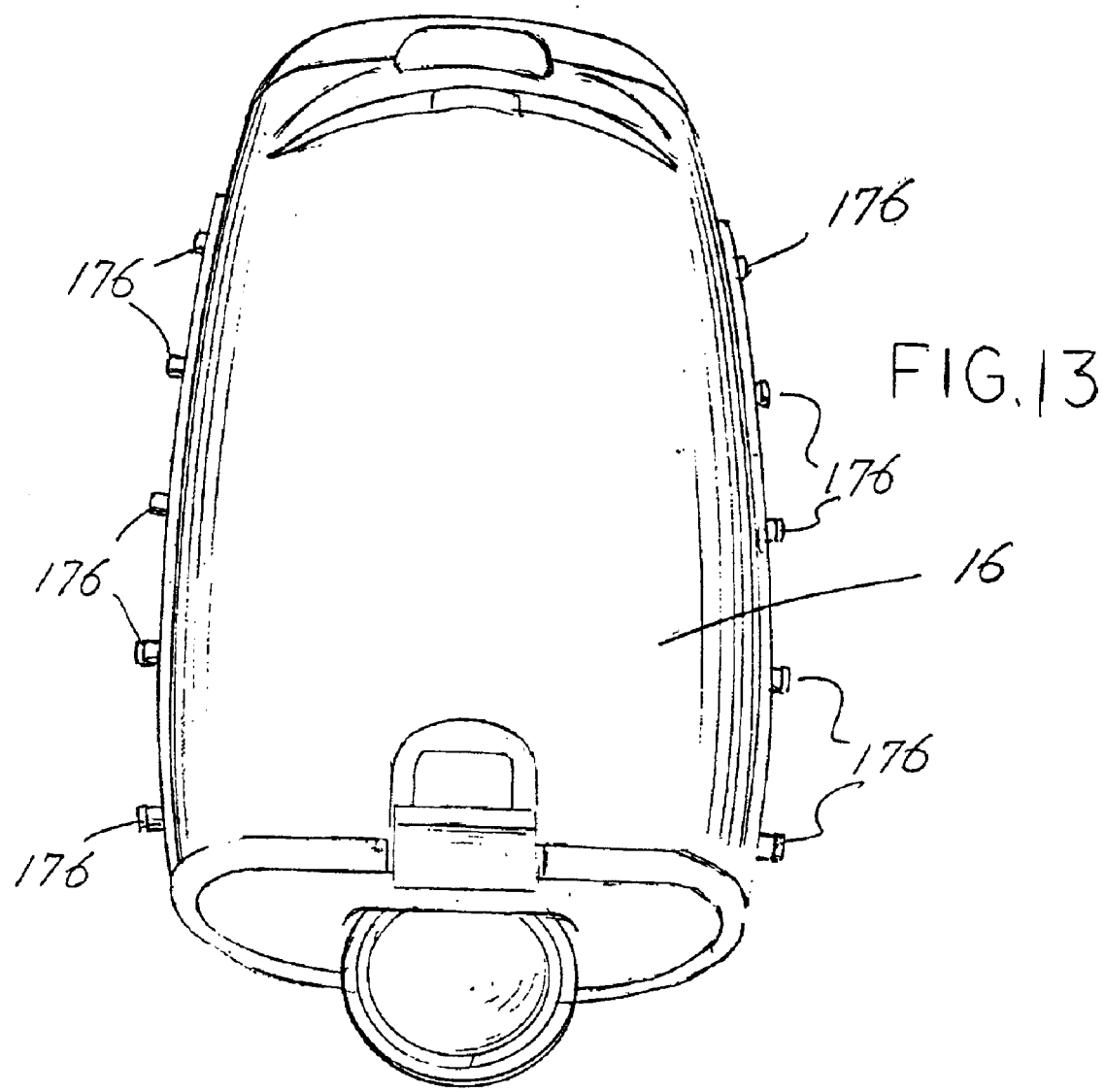

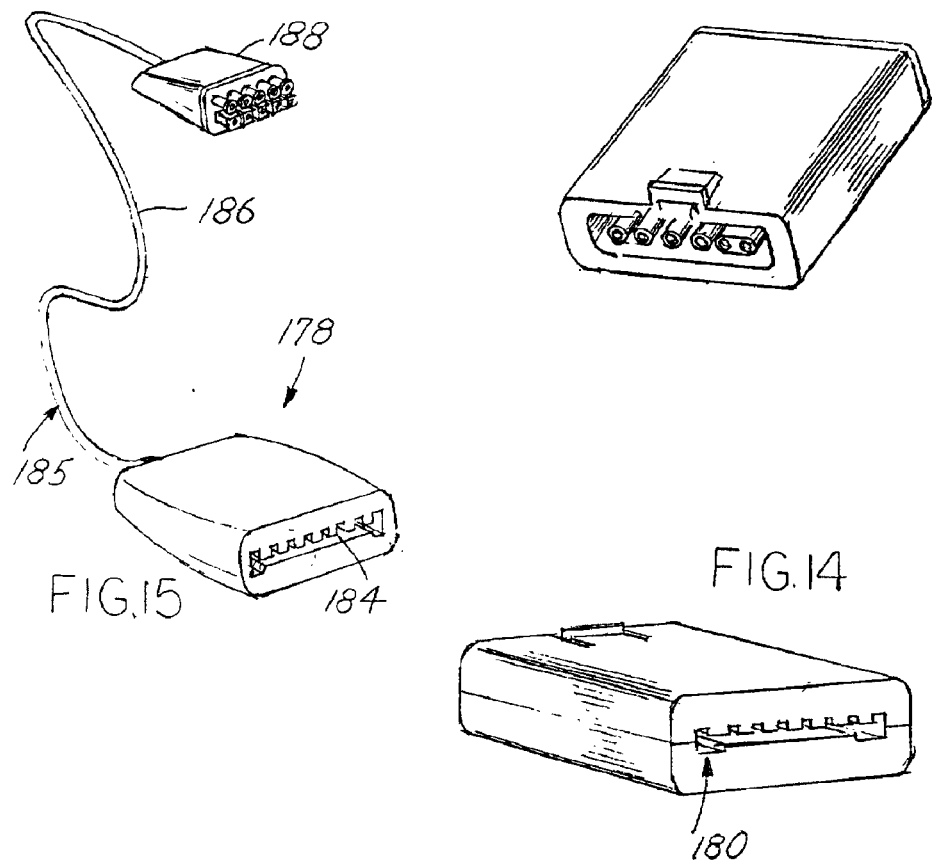
FIG.15
FIG.14
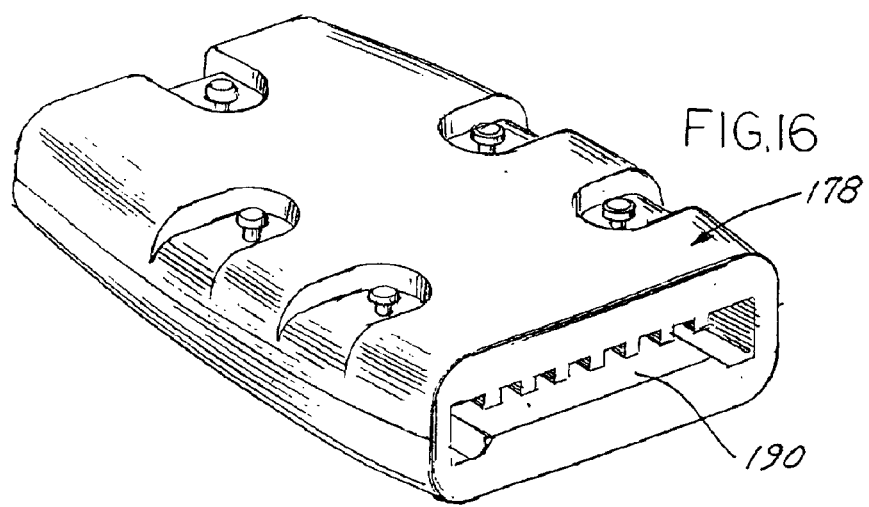
FIG.16

WIRELESS ECG SYSTEM

RELATED APPLICATIONS

This application is a continuation-in-part and claims the benefit of the filing date pursuant to 35 U.S.C. §120 application Ser. No. 09/908,509, for a WIRELESS ELECTROCARDIOGRAPH SYSTEM AND METHOD, filed Jul. 17, 2001 now U.S. Pat. No. 6,611,705, the disclosure and content of which is hereby incorporated by reference in its entirety.

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to a cardiac monitoring system and, more particularly, to a wireless electrocardiograph (ECG) system.

BACKGROUND OF THE INVENTION

An electrocardiograph (ECG) system monitors heart electrical activity in a patient. Conventional ECG systems utilize conductive pads or electrodes placed on a patient in specific locations to detect electrical impulses generated by the heart during each beat. In response to detection of the electrical impulses from the heart, the electrodes produce electrical signals indicative of the heart activity. Typically, these electrical signals are directly transferred from the electrodes to a stationary ECG monitor via multiple cables or wires. The ECG monitor performs various signal processing and computational operations to convert the raw electrical signals into meaningful information that can be displayed on a monitor or printed out for review by a physician.

Doctors have used ECG systems to monitor a patient's heart activity for decades. Currently, there are several different systems that use ECG signals to monitor a patient's heart activity. These systems, however, are generally stationary and are not developed or suitable for portable use. While portable telemetry systems exist, they are not a direct replacement for stationary ECG monitors. Moreover, because conventional systems use multiple cables or wires, and are cumbersome and uncomfortable for the patient, and require a significant amount of set up time. Thus, a need exists for an ECG system that solves the aforementioned problems.

BRIEF SUMMARY OF THE INVENTION

The present invention relates to a wireless ECG system that is universally compatible with existing or conventional ECG monitors. The ECG system comprises a chest assembly, a body electronics unit, and a base station. The chest assembly connects to electrodes specifically located on a patient's body for detecting electrical signals from the patient's heart. The electrical signals are detected by the chest assembly—thus, providing up to a "7 lead" analysis of the heart. Alternatively, the chest assembly can be augmented with a precordial assembly that connects to electrodes specifically located on the patient's body—thus, providing a "12 lead" analysis of the heart.

The electrical signals are transmitted through the chest assembly and the precordial assembly to the body electronics unit, which removably secures to the patient via an armband. The body electronics unit transmits the electrical signals to the base station via radio transmission. The base station transmits the electrical signals to a conventional ECG monitor via standard cabling, which, in turn, processes or transforms the electrical signals into meaningful information that can be displayed on the ECG monitor for review by a physician.

The ECG system eliminates the wires that ordinarily tethers an ECG patent to an ECG monitor by replacing conventional wires with a radio link. The present invention is lightweight and portable—thereby providing increased comfort and mobility to the patient. In addition, the present invention requires decreased setup times and is more convenient for health practitioners to use than conventional ECG systems.

These as well as other novel advantages, details, embodiments, features, and objects of the present invention will be apparent to those skilled in the art from the following detailed description of the invention, the attached claims and accompanying drawings, listed herein below which are useful in explaining the invention.

BRIEF DESCRIPTION OF THE DRAWING

The foregoing aspects and many of the advantages of the present invention will become readily appreciated by reference to the following detailed description of the preferred embodiment, when taken in conjunction with the accompanying drawings, wherein:

FIG. 7 is a front view of an exemplary embodiment of the body electronics unit;

FIG. 7a is an exemplary embodiment of the user interface of the electronics body unit;

FIG. 12 is a block diagram of an exemplary embodiment of the receiver;

FIG. 13 is a perspective view of an exemplary embodiment of the base station;

FIG. 14 is an exemplary embodiment of the adaptor assembly;

FIG. 15 is another exemplary embodiment of the adaptor assembly;

FIG. 16 is another exemplary embodiment of the adaptor assembly; and

DESCRIPTION OF THE PREFERRED EMBODIMENT

Figure 1:
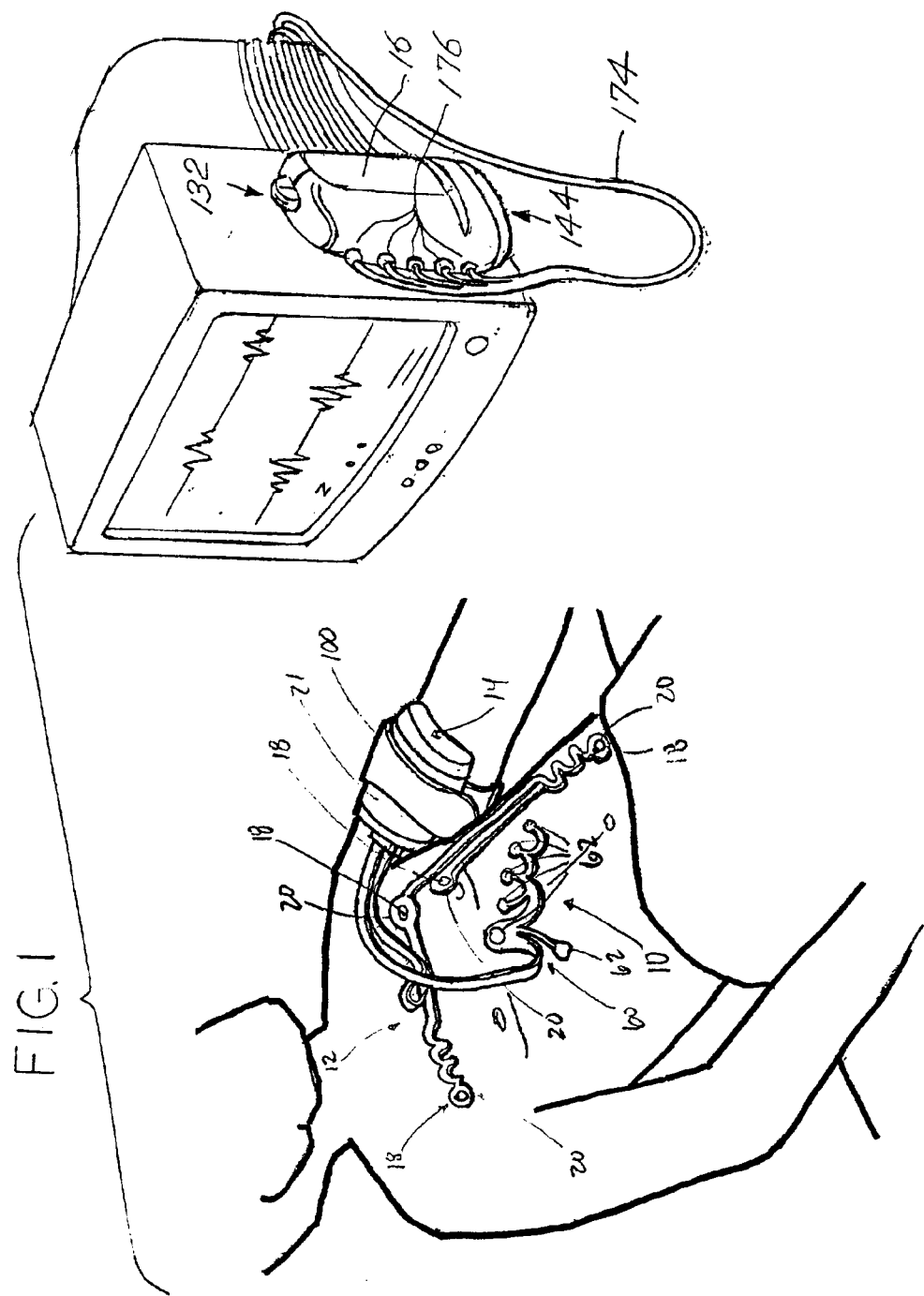
FIG. 1 is a perspective view of an exemplary embodiment of the ECG system.

For a better understanding of the present invention, reference may be had to the following detailed description taken in conjunction with the appended claims and accompanying drawings. Briefly, the present invention relates to a wireless, portable ECG system. Referring to FIG. 1, the ECG system 10 comprises a chest assembly 12, a body electronics unit 14, and a base station 16.

The chest assembly 12 is a one-piece flexible circuit that connects a plurality of electrode connectors 18, which are individually labeled 18a, 18b, 18c 18d, and 18e. The electrode connectors 18 have releasable connections that connect to electrodes 20, which are individually labeled 20a, 20b, 20c, 20d, and 20e. Preferably, the electrode connectors 18 have snap terminals that connect to electrodes 20 having snap terminals. Each electrode connector 18 connects to an electrically conductive element or trace for transmitting electrical signals. The electrically conductive elements or traces run along the chest assembly 12 and connect to a chest assembly connector 21.

Figure 2:
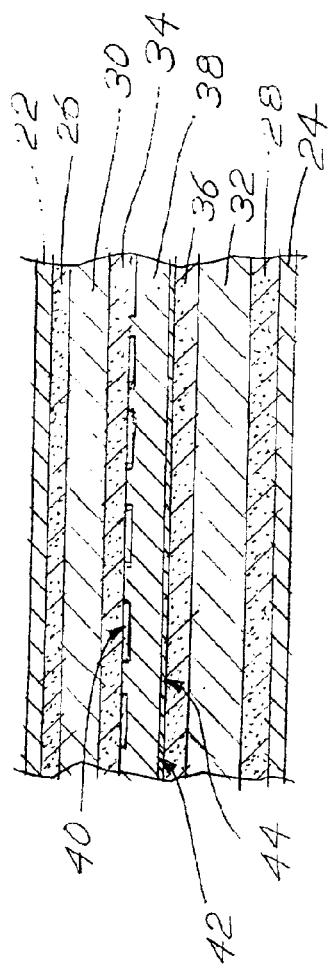
FIG. 2 is a cross sectional view of the chest assembly and the precordial assembly.

Referring to FIG. 2, the chest assembly 12 has outer layers 22, 24 that are constructed of a lightweight and reasonably moisture resistant material, such as DuPont Sontara® or other suitable fabric. Adhesive layers 26, 28 secure insulating layers 30, 32 to the outer layers 22,24 respectively. Insulating layers 30, 32 are constructed of Mylar® (polyester) film or other suitable insulating material. Adhesive layers 34, 36 secure the insulating layers 30, 32 to a base layer 38. The base layer 38 is preferably constructed of Mylar film and has a first side 40 and a second side 42. The electrically conductive elements or traces that connect to the electrode connectors 18 are located on the first side 40 of the base layer 38. One such conductive element or trace is shown at 39. A shielding layer 44 for reducing any external inferences or radio frequency noise with the chest assembly 12 is located on the second side 42 of the base layer 38. The shielding layer 44 may be constructed of single or multiple layers of dielectric, or electrically or magnetically conductive material. The back of the electrode connector 18 may also be covered with Mylar to further insulate the chest assembly 12 and prevent an externally applied electric potential from entering the ECG system. The shielding layer preferably comprises an X-patterned grid (graphically represented with hash marks on shielding layer 44 in FIG. 2.)

Referring back to FIG. 1, the chest assembly 12 attaches to five electrodes 20 and provides a means for generally positioning the electrodes on the patient, thereby providing up to a "7 lead" analysis of the electrical activity of the heart. The electrode connectors 18 are preferably labeled and color-coded to ensure that the chest assembly 12 is properly positioned on the patient and connected to the appropriate electrodes 20. For instance, the electrode connectors 18a, 18b, 18c, 18d, 18e are labeled RL, LA, LL, RA, and V, respectively. The chest assembly 12 is constructed such that the RA electrode connector is connected to an electrode positioned on the right side of the patient's chest about level of the first and second intercostal space, the LA electrode connector is connected to an electrode positioned on the left side of the patient's chest about level of the first and second intercostal space, the RL and LL electrode connectors are connected to electrodes positioned on the left side of the patient's torso, and the V electrode connector is connected to an electrode positioned in the middle of the patient's chest about level of the fourth and fifth intercostal space. The chest assembly 12 is designed such that it is centered on the chest below the patient's clavicle.

Figure 3:
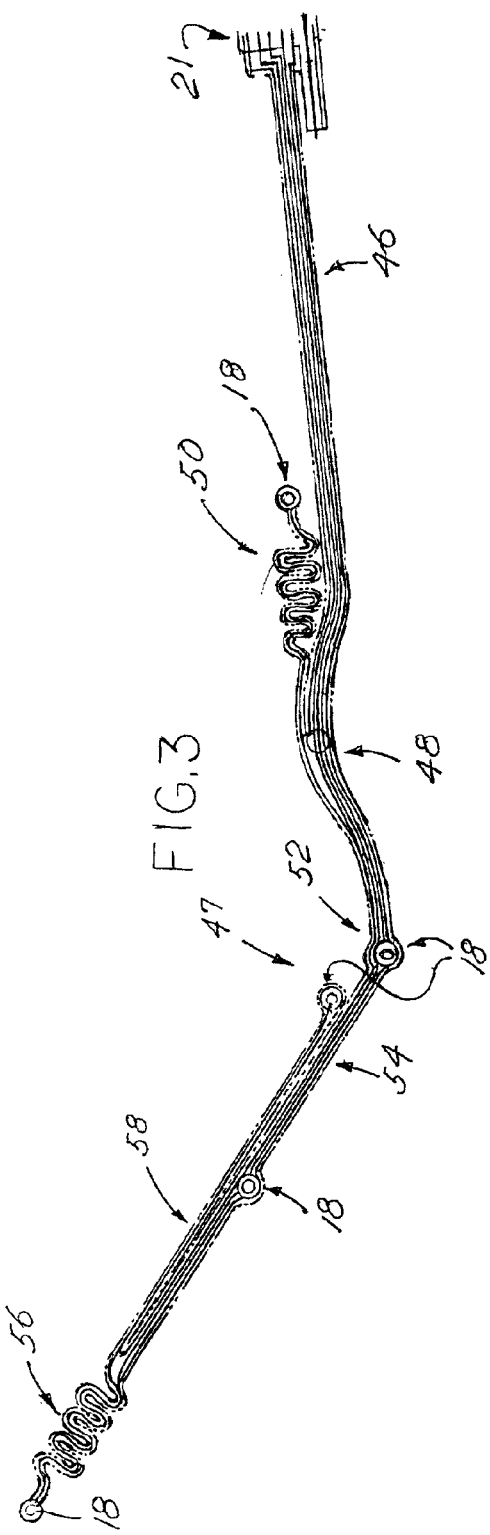
FIG. 3 is a top view of an exemplary embodiment of the chest assembly.

Referring to FIG. 3, the chest assembly 12 is configured to provide flexible positioning of the chest assembly 12 on the patient. FIG. 3 is for illustrative purposes only, and thus, the chest assembly 12, as depicted in FIG. 3, is not limited to any particular shape or configuration. The chest assembly 12 has a linear section or tail 46 extending from the chest assembly connector 21. Referring back to FIG. 1, the tail 46 has a securing means 46a which allows the tail 46 to extend to either side of the patient. This securing means 46a may be any suitable mechanical device although adhesive or a clip is most preferred. Referring back to FIG. 3, the tail 46 flows into an electrode retaining section 47. The electrode retaining section 47 has an arcuate section 48. A first expandable arm 50 attaches to the arcuate section 48. The RA electrode connector attaches to the first expandable arm 50. The arcuate section 48 flows into a transition section 52. The LA electrode connector attaches to the transition section 52. The transition section 52 flows into a linear run 54. The RL electrode connector attaches to the linear run 54. A second expandable arm 56 and an extension arm 58 attach to the linear run 54. The V electrode connector attaches to the second extension arm 58 and the LL electrode connector attaches to the second expandable arm 56.

The expandable arms 50, 56 are die cut in a serpentine pattern. The expandable arms 50, 56 comprise polypropylene or polyethylene fabric, Kapton, Mylar, or other flexible, memoryless material. The expandable arms 50, 56 expand, if necessary, by elongating the serpentine pattern. When expanded, a portion or all of the expandable arm is extended. Where only a portion of the expandable arm is extended, another portion remains folded. The expandable arms 50, 56 allow for extension as needed to so that the chest assembly 12 can fit patients of various sizes and also allow for patient movement when the patient is wearing the chest assembly 12. The extension arm 58 allows for flexible positioning of the V electrode connector in the middle of the patient's chest such as placement at electrode position V1, V2 or V3. In some instances, the health care practitioner may desire not to utilize the extension arm 58 for taking electrocardiograph measurements. Thus, to keep the extension arm 58 secured to the linear run 58 and to ensure that the extension arm 58 will not interfere with the placement and positioning of the chest assembly 12, the extension arm 58 is die cut with a perforated seam that connects the extension arm 58 and the linear run 54 along the length of the extension arm 58. If the health care practitioner desires to use the extension arm 58, the perforated seam is unbroken so that the extension arm 58 can be selectively positioned on the patient's chest.

The chest assembly 12 can be used with a precordial assembly 60 to provide a "12-lead" analysis of the electrical activity of the heart. Similar to the chest assembly 12, the precordial assembly 60 is a one-piece flexible circuit that connects a plurality of electrode connectors 62. The electrode connectors 62 have releasable connections that connect to electrodes 64. Preferably, the electrode connectors 62 have snap terminals that connect to electrodes 64 having snap terminals. Each electrode connector 62 connects to an electrically conductive element or trace for transmitting electrical signals from a patient's heart. The electrically conductive elements or traces run along the precordial assembly 60 and connect to a precordial assembly connector 66. The precordial assembly 60 has the construction as shown in FIG. 2.

As depicted in FIG. 1, the precordial assembly 60 attaches to six electrodes 64 that are selectively positioned on the abdomen and middle chest of the patient. The electrode connectors 62 of the precordial assembly 60 are preferably labeled and color-coded so as to prevent a health care provider from applying or positioning the precordial assembly onto the patient improperly. For instance, the electrode connectors 62a, 62b, 62c, 62d, 62e, and 63f are labeled V1, V2, V3, V4, V5, and V6 respectively. When the precordial assembly 60 is used, the V electrode connector on the chest assembly 12 is removed from its electrode and replaced with an electrode connector on the precordial assembly 60.

Figure 4:
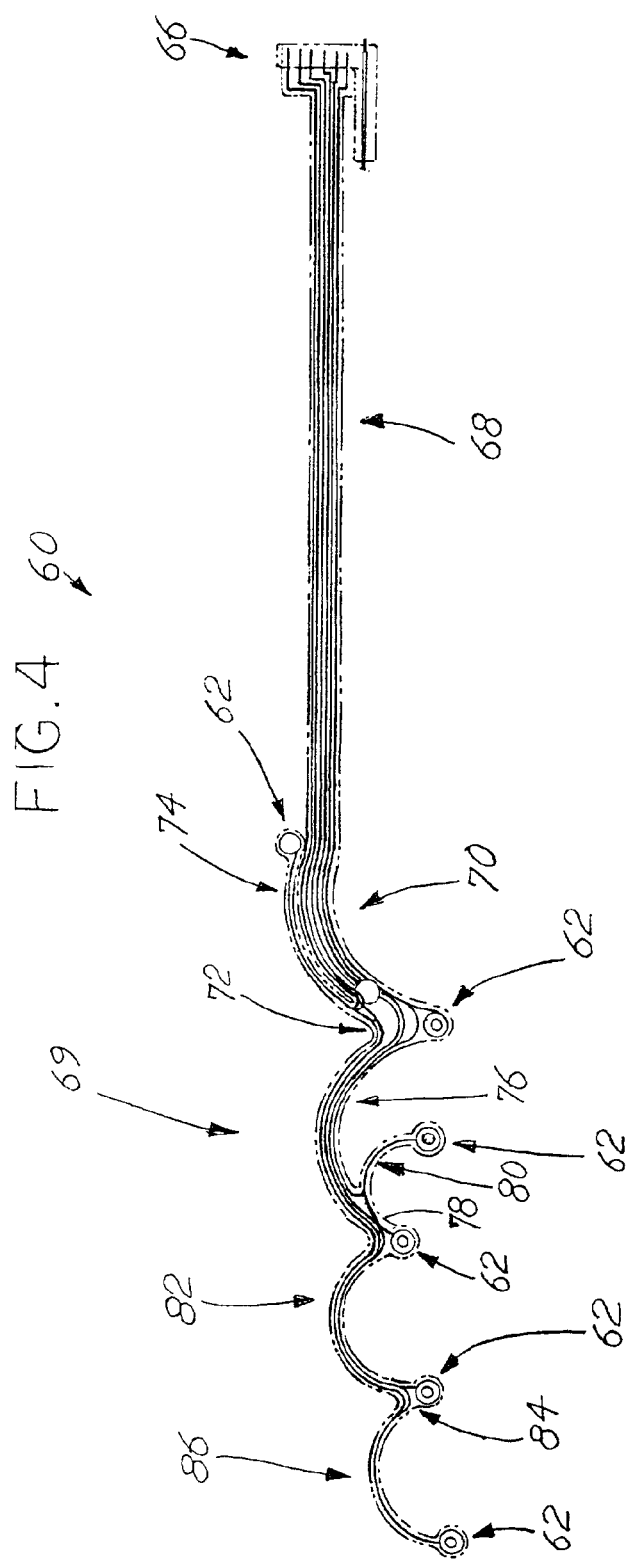
FIG. 4 is a top view of an exemplary embodiment of the precordial assembly.

As shown in FIG. 4, the precordial assembly 60 is configured to provide flexible positioning of the precordial assembly 60 on the patient. FIG. 4 is for illustrative purposes only, and thus, the precordial assembly 60, as depicted in FIG. 4, is not limited to any particular shape or configuration. The precordial assembly has a linear section or tail 68 extending from the precordial assembly connector 66. The linear section or tail 68 flows into an electrode retaining section 69. The electrode retaining section 69 has a first arcuate section 70 having a first transition section 72. The V2 electrode connector attaches to the first transition section 72. The V1 electrode connector attaches to a first extension arm 74 connected to the first transition section 72. A second arcuate section 76 extends from the first transition section 72. A second transition section 78 abuts the second arcuate section 76 and the V4 electrode connector attaches to the second transition section 76. The V3 electrode connector attaches to a second extension arm 80 connected the second transition section 78. A third arcuate section 82 flows from the second transition section 78. The third arcuate section 82 abuts a third transition section 84. The V5 electrode connector attaches to the third transition section 84. A fourth arcuate section 86 extends from the third transition section 84. The V6 electrode attaches to the fourth arcuate section 86. The configuration of the precordial assembly 60 allows the health care provider or physician to flexibly position the electrode connectors 62 as needed to properly situate the precordial assembly 60 on the patient and to allow for patient movement when the patient is wearing the precordial assembly 60.

In operation, the chest assembly 12 and the precordial assembly 60 detect electrical signals generated by the heart during each beat and transfer these signals to the body electronics unit 14. When the system is operating in "7 lead" mode (i.e. when only the chest assembly 12 is being used) the body electronics unit 14 acquires signals from the RL, RA, LL, LA, and V electrodes. The body electronics unit 14 uses the RL electrode as a ground reference. When the system is operating in the "12 lead" mode (i.e. the chest assembly 12 and the precordial assembly 60 are being used) the body electronics unit 14 acquires signals from the RL, RA, LL, and LA electrodes via the chest assembly 12 and acquires signals from the V1, V2, V3, V4, V5, and V6 electrodes via the precordial assembly 60. Alternatively, a various number of electrodes may be monitored by the system. For example, the health care provider or physician may choose to use only two electrodes to monitor the heart, seven electrodes to monitor the heart, or the like. In other words, the present system is not limited to performing a "7 lead" and "12 lead" analysis of the heart. In addition, to detecting electrical signals from the heart, the chest assembly 12 and the precordial assembly 60 may be constructed to detect other vital signs of the patient, for example, pulse, respiration rate, heart rate, temperature EEG signals, and pulse oximeter signals.

Figure 5:
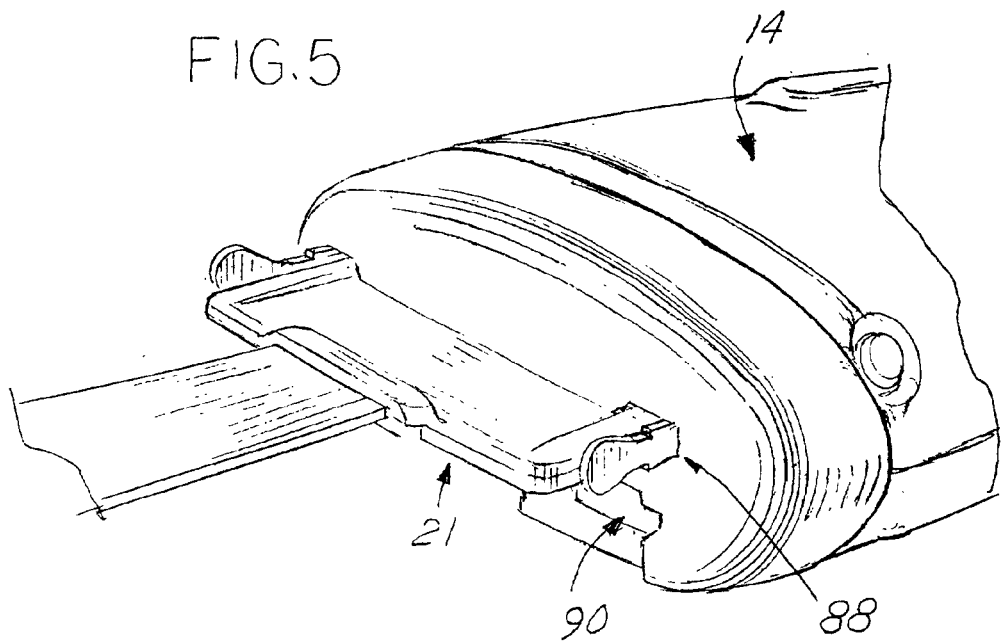
FIG. 5 is a perspective view of an exemplary embodiment of the body electronics unit.

Referring to FIG. 5, the chest assembly 12 connects to the body electronics unit 14 via a chest assembly connector 21. Specifically, the chest assembly connector 21 inserts into a chest assembly port 88 located in the body electronics unit 14. Similarly, the precordial assembly 60 connects to the body electronics unit 14 via the precordial assembly connector 66. Specifically, the precordial assembly connector 66 (not shown) inserts into a precordial assembly port 90. Resisters are connected to the chest assembly port 88 and the precordial assembly port 90 to prevent excessive electrical current from entering the body electronics unit 14—thereby ensuring that the body electronics unit 14 continues to operate properly in the presence a strong electrical current caused by a defibrillator (i.e. a 5 kV defibrillation excitation). The chest assembly connector 21 and the precordial assembly connector 66 are specifically keyed or configured to prevent the assembly connectors 21, 66 from being inserted into the assembly ports 88, 90 backwards, misaligned or otherwise improperly. Moreover, the chest assembly connector 21 is keyed or configured such that it is not compatible with the precordial assembly port 90. Likewise, the precordial assembly connector 66 is keyed or configured such that it is not compatible with the chest assembly port 88. Specifically, as shown in FIG. 5A, the chest assembly connector 21 has tongues 21a specifically configured or arranged to fit into corresponding grooves 21b of the chest assembly port 88. Accordingly, the chest assembly connector 21 can only be connected to the chest assembly port 88 in one orientation. For example, if the tongues 21a are not aligned with the grooves 21b, the chest assembly connector 21 will not couple to the chest assembly port 88. Likewise, the precordial assembly connector 66 has tongues (not shown) specifically configured or arranged to fit into corresponding grooves (not shown) of the precordial assembly port 90.

Figure 6:
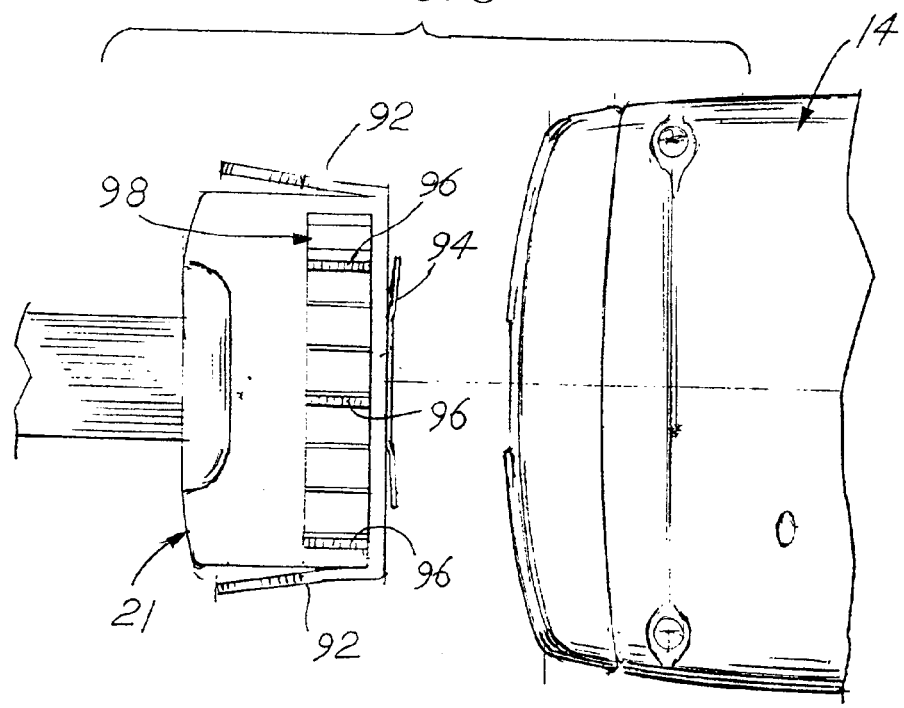
FIG. 6 is a top view an exemplary embodiment of the assembly connectors.

As shown in FIG. 6, the chest assembly connector 21 and the precordial assembly connector 66 (not shown) have retaining clips or flanges 92 located on the sides of the connectors 21, 66 for removably securing the connectors 21, 66 into the assembly ports 88, 90. However, other means may be used to removably secure the connectors 21, 66 in the assembly ports 88, 90, such as screws, pins or the like. In addition, the assembly connectors 21, 66 may have spring flanges or clips 94 located at the tip of the connectors 21, 66 for providing a bias or tension against the assembly ports 88, 90. The spring flanges or clips 94 provide the connectors 21, 66 with a secure fit within the assembly ports 88, 90, thereby reducing any play or movement of the connectors 21, 66 within the assembly ports 88, 90. The electrically conductive elements or traces are specifically configured on the connectors 21, 66 so as to ensure that the electrical signals from the heart are properly transmitted to the body electronics unit 14. In other words, the electrically conductive elements or traces must be sufficiently spaced apart or otherwise isolated in some manner to prevent arcing across the electrically conductive elements. In addition, the spacing of the electrically conductive elements or traces permits the chest assembly and the precordial assembly to withstand defibrillation shock. Furthermore, the connectors 21, 66 have ribs 96 for preventing the electrically conductive elements or traces from coming into contact with metal objects or the like when the connectors 21, 66 are not inserted into the assembly ports 88, 90.

The chest assembly connector 21 has a sensor pin or ground pin 98 that completes a circuit within the body electronics unit 14 when the chest assembly connector 21 is plugged into the chest assembly port 88, thereby activating the power and bringing the body electronic unit 14 out of "sleep mode." The sensor pin has specific tongue that corresponds and fits into a groove located in the chest assembly port 88. The sensor pin 98 serves as a means for the body electronics unit 14 to identify the chest assembly 12 and to prevent the use of other chest assemblies or electrocardiograph wearables that are not designed to be used with the on-body electronic unit 14. In other words, the power of the body electronics unit 14 will not activate unless the body electronics unit 14 identifies or recognizes the sensor pin 98 of the chest assembly 12.

The outside casing of the body electronics unit 14 is constructed of lightweight, molded plastic, such as acrylonitrile-butadiene-styrene (ABS) or other suitable material. The shape and configuration of the body electronics 14 unit is not limited to any particular shape or configuration. As shown FIG. 1, the body electronic unit 14 removably secures to the patient's arm via an armband 100, thus making the body electronics unit 14 readily accessibly to the patient. The armband 100 wraps around either the patient's right or left arm and attaches via Velcro or other suitable fastening means such as pins, snaps, or the like. The body electronics unit 14 slides under a strap or pocket on the armband 100. Referring to FIG. 7, the body electronic unit 14 has a user interface 102 and a battery 104. The user interface 102 provides information to the patient pertaining to the system's operating status or functionality. For example, an exemplary embodiment of the user interface 102 may provide information on whether the body electronics unit 14 is communicating or transmitting normally to the base station 16, whether the battery 104 of the body electronics unit 14 is charging or the battery 104 is low, whether the power of the body electronics unit 12 is activated, or whether the body electronics unit 14 or base station is malfunctioning. In addition the user interface 102 may provide instructions on the correct order or procedure for pairing or coupling the body electronics unit 14 with the base station 16. Such information may be communicated to the patient via the user interface 102 in various ways, for example, LEDs, LCD, text, audible tones, etc. An exemplary embodiment of the user interface is shown in FIG. 7a. The user interface 102 is readily accessible to the patient when the body electronics unit 14 is secured to the armband 100.

The battery 104 is inserted into a battery port 106 located in the bottom of the body electronics unit 14. The battery 104 is retained in the battery port 106 by latches or other suitable fastening means, such as clips, screws or the like. The battery 104 is preferably a 3.6 V Li-ion rechargeable battery. The battery 104 is readily accessible to the patient when the body electronics unit 14 is secured to the armband 100.

The body electronics unit 14 controls the acquisition of the ECG signals from the chest assembly 12 and the precordial assembly 60. A transmitter 108 within the body electronics unit 14 receives or acquires ECG signals from the chest assembly 12 and the precordial assembly 60 preferably at 3 kbps. When the system is operating in "7 lead" mode (i.e. when only the chest assembly 12 is being used) the body electronics unit 14 acquires signals from the RL, RA, LL, LA, and V electrodes. When the system is operating in the "12 lead mode" (i.e. the chest assembly 12 and the precordial assembly 60 are being used) the body electronics unit 14 acquires signals from the RL, RA, LL, and LA electrodes via the chest assembly 12 and acquires signals from the V1 thru V6 electrodes via the precordial assembly 60. In addition, other vital signs of the patient may be detected by the system and transmitted to the body electronics unit 14, for example pulse, respiration rate, heart rate, temperature, EEG signals and pulse oximeter signals.

Figure 8:
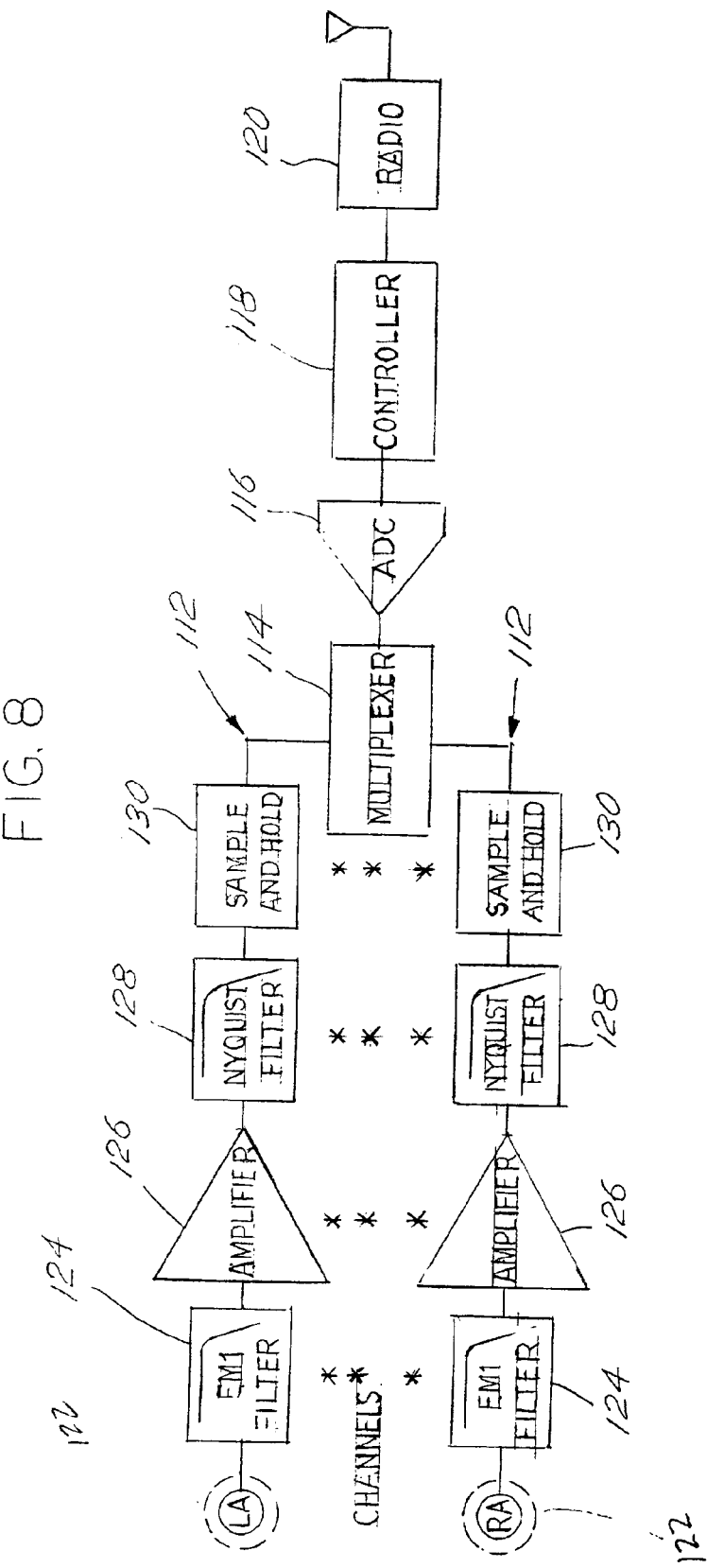
FIG. 8 is a block diagram of an exemplary embodiment of the transmitter.

As shown in FIG. 8, the transmitter 108 comprises an application specific integrated circuit, a processor or other circuit 110, a plurality of signal channels 112, a multiplexer 114, an analog-to digital converter (ADC) 116, a controller 118, and a radio 120. Additionally, fewer or different components can be used. The body electronics unit 14 has nine signal channels 112 corresponding to the ten electrodes connected to the chest assembly 12 and the precordial assembly 60. The electrode channels 112 each comprise a connector 122, a filter 124, an amplifier 126, a Nyquist filter 128 and a track and hold circuit 130. The connectors 122 of the signal channels 112 connect to either the chest assembly port 88 or the precordial assembly port 90, depending on whether the electrode channel 112 corresponds to an electrode located on the chest assembly 12 or the precordial assembly 60. The filter 124 comprises a low pass filter, such as for removing electromagnetic interference signals. The amplifier 126 amplifies the signals from the electrodes. The Nyquist filter 128 comprises a low pass filter for removing out-of-band high frequency content of the amplified signals to avoid sampling error. The track and hold circuit 130 enables the system to sample all nine electrode channels signals 112 at a same or relative times so that there is not differential error created when these signals are combined later in an ECG monitor.

The multiplexer 114 sequentially selects signals from the electrode signal channels 112 using time division multiplexing. One of ordinary skill in the art, however, recognizes that other combination functions can be used. The ADC 116 converts the combined analog signals to digital signals for transmission. Preferably the controller 118 comprises a digital signal processor (DSP) that decimates the digitized signals as to lessen the bandwidth required to transmit the signals. The radio 120 modulates the digital signals with a carrier signal for transmission. In an exemplary embodiment, the radio 120 includes a demodulator for receiving information. The controller 118 digitally transmits the ECG data to the base station 16. In addition to transmitting ECG data, the controller 118 may transmit signals pertaining to pacemaker information, battery level information, electrode disconnection information, and other information as required. For example, vital signs such as pulse, respiration rate, heart rate, temperature, EEG signals, and pulse oximeter signals may be transmitted.

The body electronics unit continuously monitors the integrity of all patient electrode connections. In the event a lead is disconnected, the body electronics unit will send a signal to the base station which in turn causes the base station to trigger the "lead off" alarm on the ECG monitor. Additionally, the body electronics unit has a self-test function which monitors the integrity of the primary functions including the microprocessor, data acquisition, internal voltage references, and radio functionality. In the event a failure is detected, the body electronics unit will capture the fault condition, stop data acquisition and transmission and indicate that fault has occurred through the lead off alarm.

The body electronics unit 14 operates to minimize undesired noise or signals. For example, components are matched such that later application to a differential amplifier in a legacy ECG monitor for determining a heart vector is accurate. ECG vectors are not formed by the ECG system 10, but rather by the legacy ECG monitor. Because the ECG system 10 is essentially "in-series" with the legacy ECG monitor, any error may produce undesirable results. One potential source of error is differential error. This differential error can be observed on the legacy ECG monitor when the ECG monitor forms the ECG lead signals by combining the individual electrode signals in the ECG monitor input stage. This input stage comprises a difference, or differential, amplifier to eliminate common mode interference from the signals produced at the electrodes 20.

An artifact will be present if there is any difference in how each of the electrode signals are processed when the legacy ECG's differential amplifier forms the ECG lead signals or ECG vectors. For example, if there is a difference in the gain of the amplifier, a difference in the phase shift associated with the anti-aliasing (Nyquist) filters, or a difference in how the respective track and hold circuits treat the electrode signals, then this differential error creates an artifact on the legacy ECG monitor. One important technique to minimize this potential source of differential errors is to choose a Nyquist filter cutoff frequency that is very high. This is because each individual filter will have differing group delay performance. To mitigate that difference, the frequency that this group delay will affect is much higher than the frequency of the ECG signals, which are about 0.05 Hz to 150 Hz. By choosing a high cutoff frequency for the Nyquist filters, any mismatch in the Nyquist filter components will not affect accuracy of the individual electrode ECG signals. For example, picking a filter cutoff frequency of 1,200 Hz mitigates this source of error. With this approach, the individual electrode ECG signals are over sampled at about 3,000 Hz in order to not introduce aliasing. Of course higher filter cutoff frequencies and correspondingly higher sampling rates may further reduce error. Lower cutoff frequencies and/or sampling rate may be used.

Figure 9A:
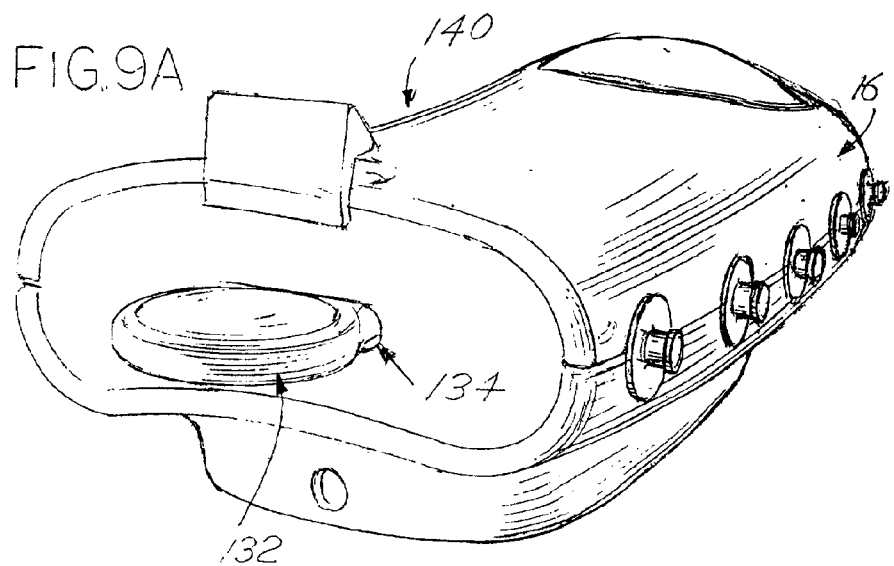
FIG. 9a is a perspective view of an exemplary embodiment of the base station used in conjunction with the token key.
Figure 9B:
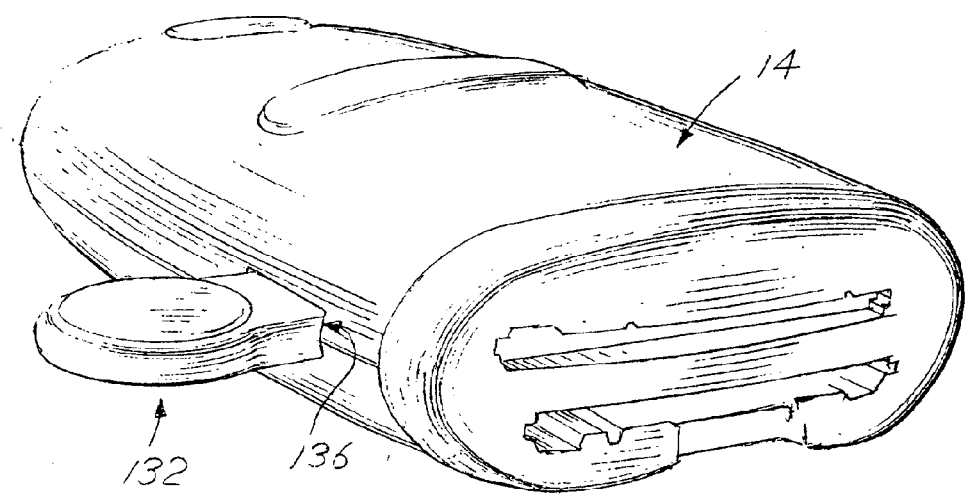
FIG. 9b depicts the body electronics unit used in conjunction with the token key.

Because the electrode signals are now sampled at such a high rate, these signals may be decimated to minimize the required transmission bandwidth. For example the digital samples are decimated by a factor of eight in the controller 118. Greater or lesser rates of decimation can be used, such as decimation as a function of the bandwidth available for transmission, the number of electrode signals to be represented, and the Nyquist sampling rate. Referring back to FIG. 1, the base station 16 receives the transmitted signals sent from the body electronics unit 14. The signals are transmitted as radio or other signals modulated with a carrier signal. Various air-interfaces can be used for transmission, such as Bluetooth or IEEE 802.11b. To establish proper communication between the body electronics unit 14 and the base station 16, the base station 16 and body electronics unit 14 need to be paired such that the base station 16 and the body electronics unit 14 only recognize signals from the its pair. This may be accomplished in number of ways including direct connection of the base station 16 and the body electronics unit 14. Preferably, a token key 132 is used to pair or radio frequency link the body electronics unit 14 and the base station 16. Referring to FIG. 9a, the token key 132 has memory chip and may optionally have a plurality of tongues or pins 133 that fit within grooves located in a token key port 134 of the base station 16 and within grooves of a token key port 136 of the body electronics unit 14. As shown in FIG. 9b, the token key 132 inserts into the token key port 134 of the base station and reads and records an identification number for the base station 16. The token key 132 is then removed from the token key port 134 and inserted into the token key port 136 located in the body electronics unit 14. The electronics unit 14 receives the identification number for the base station 16 from the token key 132. In turn, the token key 132 reads and records the identification number for the body electronics unit 14. The token key 132 is then removed from the body electronics unit 14 and reinserted into the token key port 134 of the base station 16 whereby the base station 16 confirms the presence of its own identification number on the token key 132 and also reads the identification number for the body electronics unit 14 from the token key 132. The body electronics unit 14 and the base station 16 are paired. Alternatively, pairing or coupling can be accomplished by first inserting the token key 132 into the body electronics unit 14, removing the token key 132 and inserting the token key 132 into the base station 16, removing the token key 132 and reinserting the token 132 into the body electronics unit 14. In other words, the order in which the token key 132 is inserted into the body electronics unit 14 and the base station 16 is not critical to the proper operation of the system. Referring back to FIG. 7, the user interface 102 may provide the user or health care provider with instructions on the correct order for pairing the body electronics unit 14 with the base station 16. The use of the token key 132 allows the pairing function to occur while the body electronics unit 14 is worn by the patient. This feature eliminates the need to disconnect and reconnect the body electronics unit 14 when a patient needs to be connected to different ECG monitors as a result of being moved around a hospital. The patient's body electronics unit 14 is just repaired with a new base station using the token key 132.

After the body electronics unit 14 and the base station 16 are paired, the body electronics unit 14 and the base station 16 will remain communicating with each other as long as the token key 132 remains in the token key port 134 of the base station 16 (or the token key port 136 of the body electronics unit 14, depending on the order of the pairing process). In other words, as soon as the token key 132 is removed from the base station 16, the electronics unit 14 and the base station 16 will discontinue or cease communication. Any specific token key 132 can be used to pair any specific base station 16 with any specific body electronics unit 14.

Figure 10:
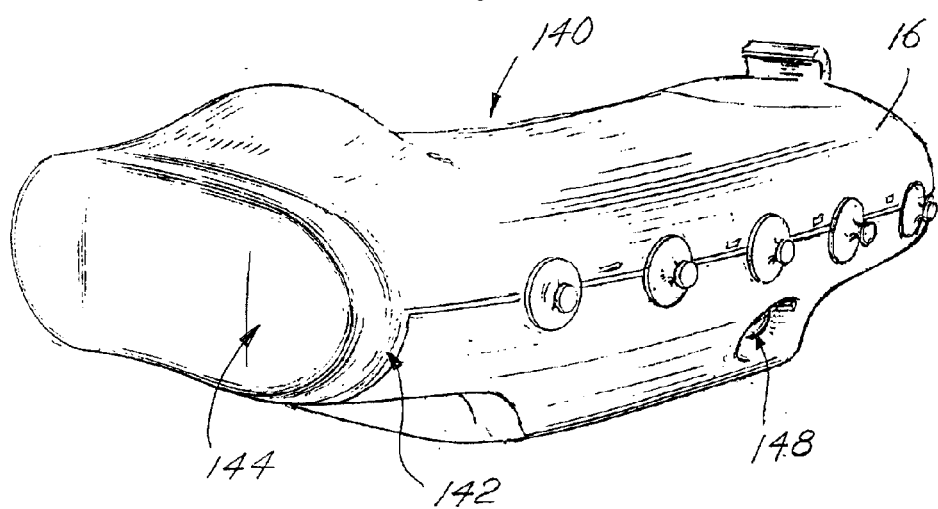
FIG. 10 is a perspective view of an exemplary embodiment of the base station.

The outside casing of the base station 16 is constructed of lightweight, molded plastic, such as acrylonitrile-butadiene-styrene (ABS) or other suitable material. The shape and configuration of the base station 16 is not limited to any particular shape or configuration. The base station 16 is removably secured to an ECG monitor 138 via suitable mounting means, such as Velcro®, dual-lock strips, double-sided foam tape, or the like. Preferably, the base station 16 is removably mounted to a mounting plate secured near the ECG monitor 138 via suitable mounting means. As shown in FIG. 10, the base station 16 has a cradle 140 for storing the body electronics unit 14 when the body electronics unit 14 is not in use or otherwise off the patient. In addition, the base station 16 has a battery port 142 in which a base station battery 144 is removably inserted. The base station 16 may be constructed to have a plurality of battery ports that store and charge batteries when the batteries are not being used. When the base station 16 is not plugged into an AC wall power inlet, the base station battery 144 provides power to the base station 16. When the base station 16 is operating on AC wall power, the base station 16 charges the base station battery 144 when the base station battery 144 is in the battery port 142. The base station 16 has a power switch 146 that activates/deactivates the power to the base station 16 and a power cord connection 148 for connecting a power cord to an AC wall power inlet. The base station battery 144 is preferably a 3.6 V Li-ion rechargeable battery.

Accordingly, the base station battery 144 and the body electronics unit battery 104 are preferably identical and interchangeable, such that each battery can be used in either the body electronics unit 14 or the base station 16. The system is designed such that a discharged body electronics unit battery 104 is swapped for a charged base station battery 144. In this manner a charged battery is always readily available for the body electronics unit. In addition, the base station 16 has a lead switch 150 that allows the health care provider to instruct the base station 16 to operate in "7 lead" mode or "12 lead" mode.

Figure 11:
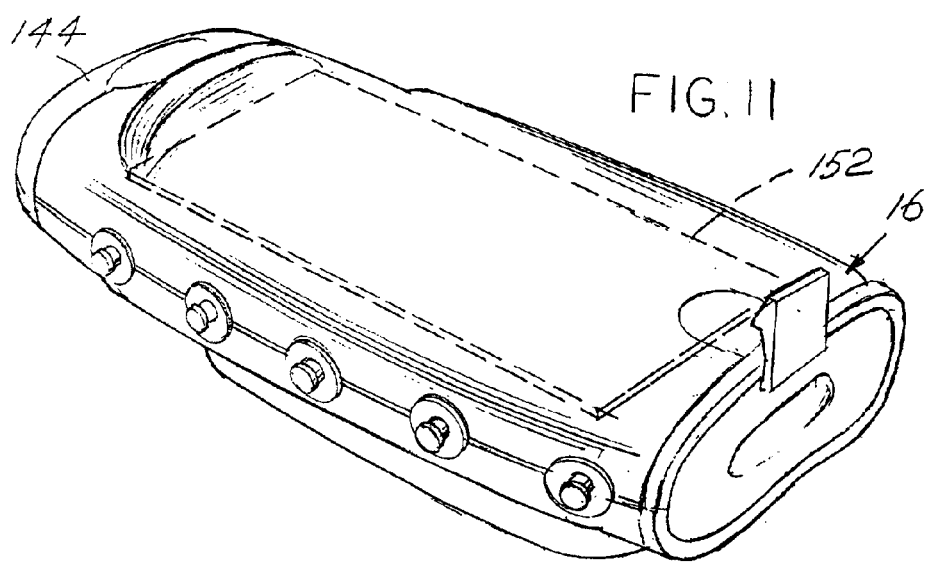
FIG. 11 is a front view of an exemplary embodiment of the base station.
Figure 11A:
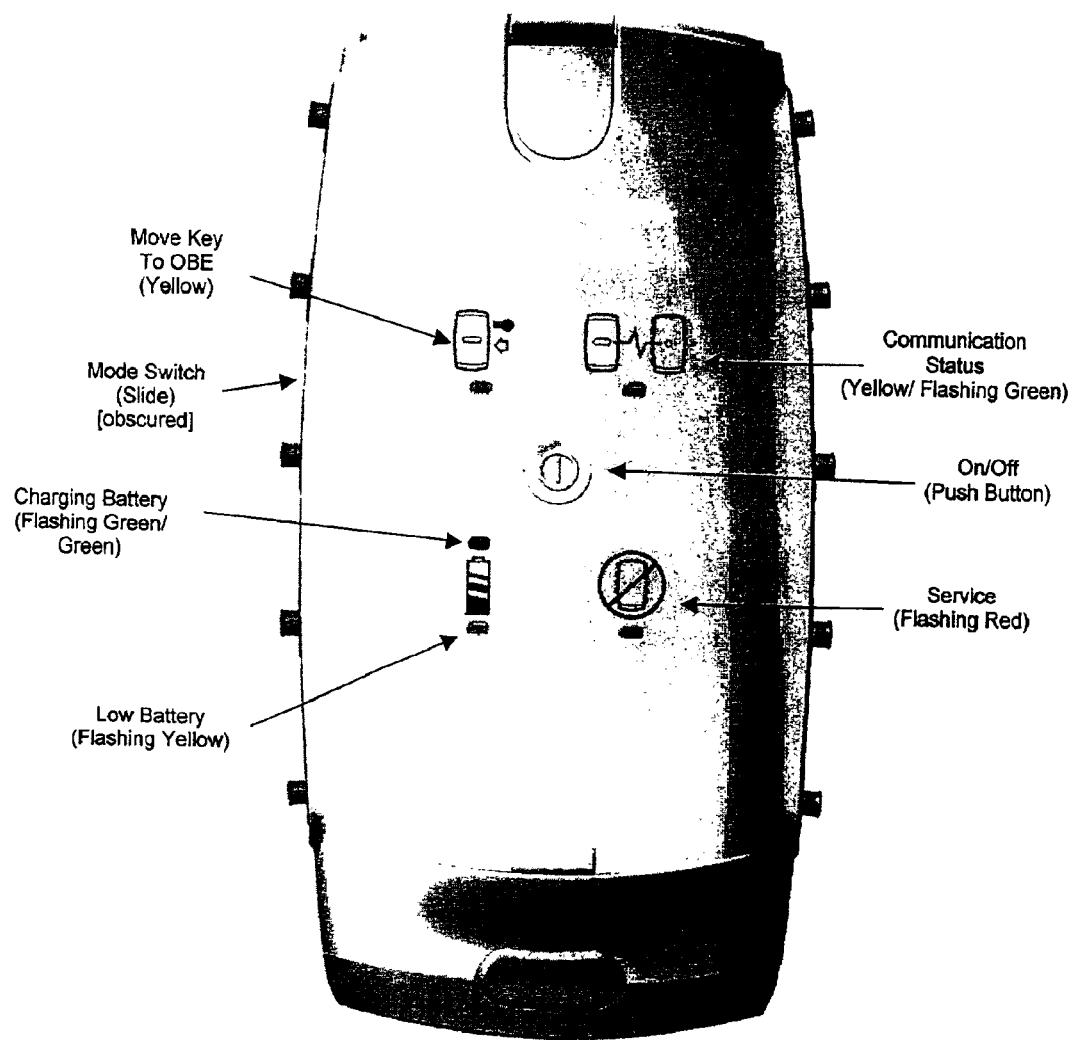
FIG. 11a is an exemplary embodiment of the user interface of the base station.

As depicted in FIG. 11, the base station 16 has a user interface 152 that provides information to the health provider or patient pertaining to the system's operating status or functionality. For example, the user interface 152 may provide information on whether the body electronics unit 14 is communicating or transmitting normally to the base station 16, whether the base station battery 144 is charging or the battery 144 is low, whether the body electronics unit battery 104 is low, or whether the power of the base station 16 is activated, whether the base station 16 is malfunctioning or otherwise requires servicing. In addition the user interface 102 may provide instructions on the correct order or procedure for pairing or coupling the body electronics unit 14 with the base station 16. Such information may be communicated to the health care provider or patient via the user interface 152 in various ways, for example, LED's, LCD, text, audible tones, etc. An exemplary embodiment of the user interface 102 is shown in FIG. 11a.

Additionally, the base station has a self-test function which monitors the integrity of the primary functions including the microprocessor, data acquisition, internal voltage references, and radio functionality. In the event a failure is detected, the body electronics unit will capture the fault condition, stop data acquisition and transmission and indicate that fault has occurred through the lead off alarm.

A receiver 154 located within the base station 16 receives signals sent to the base station 16 from the body electronics unit 14. As shown in FIG. 12, the receiver 154 includes a radio 156, a controller 158, a digital-to-analog converter (DAC) 160, a demultiplexer 162, a transceiver 164, and a plurality of electrode signal channels 166. The radio 156 demodulates the received signals for identifying digital data representing the combined electrode signals. In an exemplary embodiment, the radio 156 includes a modulator for transmitting control information. The controller 158 controls operation of the various components and may further process the signals from the radio 156, such as interpolating data, converting the signals to digital information, generating control signals for the transmitter 108 in the electronics unit 14, operating any user output or input devices, and diagnosing operation of the ECG system. Preferably, the controller 118 interpolates the electrode signals to return the effective sample rate to about 3 kHz or another frequency. This enables the reconstruction filters to have a cutoff frequency many times the bandwidth of the electrode signals, thus minimizing any differences in group delay at the frequencies of interest, i.e. less than 150 Hz. The DAC 160 converts the digital signals to analog signals. The demultiplexer 162 separates the individual regenerated electrode signals onto the separate electrode signal channels 166. The transceiver 164 operates operable pursuant to the Bluetooth specification for two-way communication with the transmitter 108.

The receiver 154 has nine electrode signal channels 166 corresponding to the 10 electrodes connected to the chest assembly 12 and the precordial assembly 60. The electrode signal channels 166 each comprise a sample and hold circuit 168, a filter 170, and an attenuator 172. The sample and hold circuit 168 is controlled by the controller 118 so that the converted electrode signals appear simultaneously on each electrode signal channel 166. Other embodiments may include individual DAC's that provide the signal substantially simultaneously. The filter 170 comprises a low pass reconstruction filter for removing high frequency signals associated with the DAC conversion process. The attenuator 172 comprises an amplifier for decreasing the amplitude to a level associated with signals at the electrodes, which were earlier amplified in the amplifiers of the body electronics unit 14. This results in a unity system gain so as not to introduce error between the electrodes and the conventional ECG monitor.

The base station 16 transmits the ECG signals to the ECG monitor 138 via preexisting or conventional monitor cables 174. In turn, the information is displayed on the ECG monitor and reviewed by a physician. As depicted in FIG. 13, the monitor cables 174 removably insert onto snap terminals 176 located on the base station 16. Preferably, the base station 16 has ten snap terminals 176 arranged on the left and right side of the base station 16. The snap terminals 176 and the monitor cables 174 are preferably labeled and color-coded so that the monitor cables 174 are properly connected to the base station 16. For instance, the five snap terminals 176 located on the left side of the base station 16 and the monitor cable 174 may be labeled as RL, LA, LL, RA, and V/V1. In addition, the five snap terminals 176 on the right side of the base station 16 and the monitor cable 174 may be labeled V2, V3, V4, V5, and V6. When the ECG system is operating in "7 lead" mode (i.e. only the chest assembly 12 is used) the monitor cable 174 is plugged into the five snap terminals 176 on the left side of the base station 16. When the ECG system is operating in "12 lead" mode (i.e. both the chest assembly 12 and the precordial assembly 60 is used) both the monitor cables 174 are plugged into the snap terminals 176—the top four snap terminals 176 on the left side of the base station 16 will be used for chest assembly electrodes and the remaining six snap terminals 176 will be used for precordial assembly electrodes.

There may be instances where a base station 16 will not be in every ward or hospital room for use with the body electronics unit 14. In such instances, an adapter assembly 178 may be used to connect the chest assembly 12 or the precordial assembly 60 to the ECG monitor 138. In one exemplary embodiment, the adaptor assembly 178 allows the chest assembly 12 or precordial assembly 60 to be plugged directly into a conventional or existing telemetry transmitter. FIG. 14 depicts the adapter assembly 178 having an assembly receptacle 180 that connects to the chest assembly 12 or the precordial assembly 60 and a telemetry box receptacle 182 that connects to a conventional or existing telemetry transmitter. In another exemplary embodiment, the adaptor assembly 178 allows the chest assembly 12 or precordial assembly 60 to be plugged directly into a conventional or existing ECG monitor trunk cables. FIG. 15 depicts the adaptor assembly 178 having an assembly receptacle 184 for connecting to the chest assembly 12 or the precordial assembly 60 and a cable assembly 185 for connecting to a conventional or existing ECG monitor trunk cable. The cable assembly 185 has a cable 186 that connects to a trunk cable adaptor 188 for connecting to an ECG monitor trunk cable. In another exemplary embodiment, the adaptor assembly 178 allows the chest assembly 12 or precordial assembly 60 to be plugged directly into standard lead wires that connect to an ECG monitor. FIG. 16 depicts the adaptor 178 having an assembly receptacle 190 for connecting to the chest assembly 12 or the precordial assembly 60 and a lead wire cable assembly 192 for connecting to a lead wire assembly. The cable assembly 192 has a cable 194 that connects to a lead wire adaptor 196 for connecting to standard lead wires. Various configurations of the adapter 178 are possible depending on the connector configuration of the standard lead wires.

Figure 17:
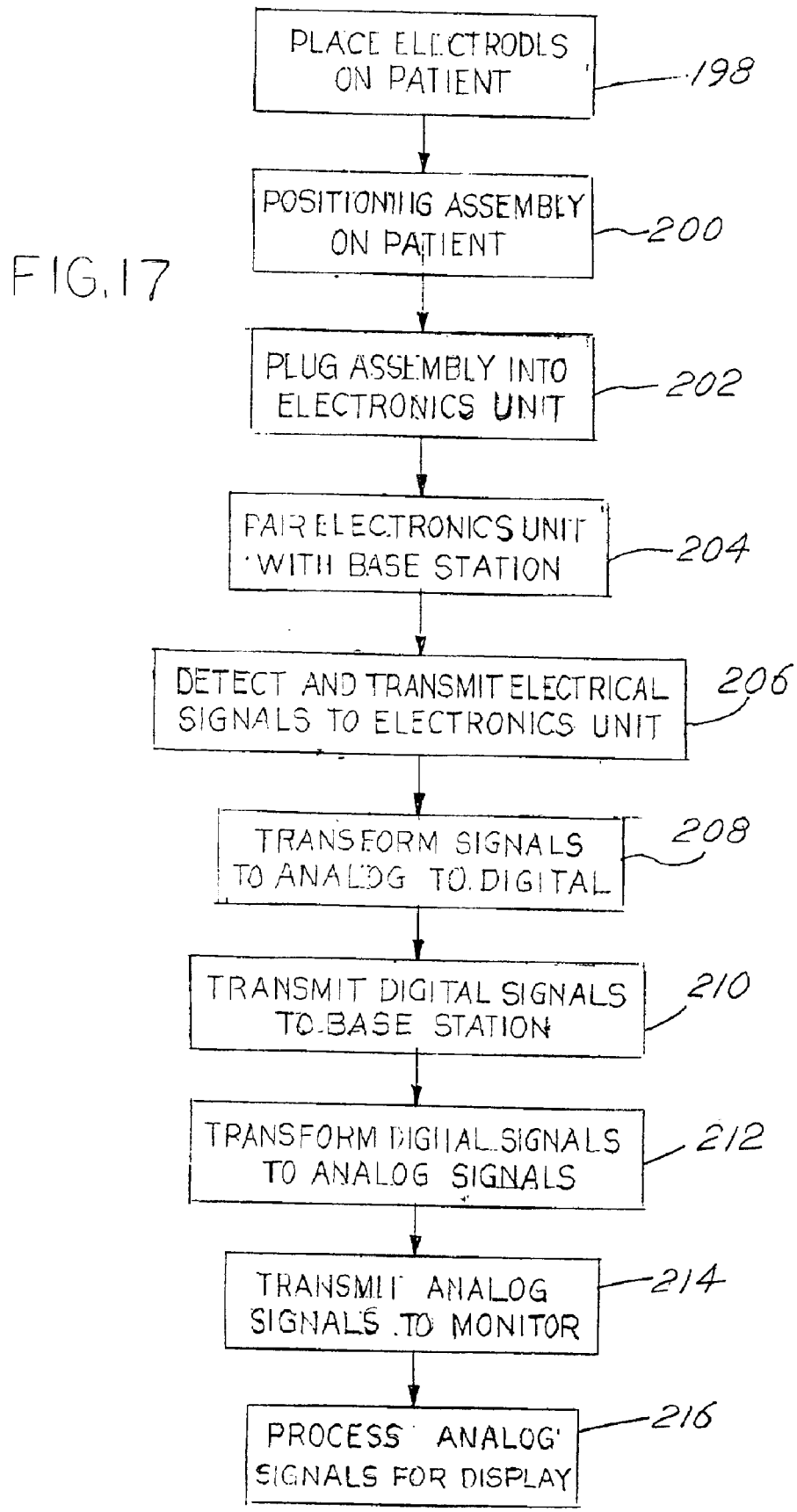
FIG. 17 is a flow chart of an exemplary embodiment for operation of the ECG system.

FIG. 17 depicts the method of monitoring the cardiac activity in the patient's heart using the wireless ECG system of the present invention. In step 198, electrodes are placed on the patient's body. In step 200, the chest assembly 12 and/or precordial assembly 60 are positioned on the patient's body by connecting the electrode connectors 21, 62 to the electrodes. In step 202, the chest assembly 12 and/or the precordial assembly 60 are plugged into the body electronics unit 14. In step 204, the electronics unit 14 and the base station 16 are paired or coupled by inserting the token key 132 into the base station 16, removing the token key 132 from the base station 16, inserting the inserting the token key 132 into the body electronics unit 14, removing the token key 132 from the electronics unit 14, and reinserting the token key 132 into the base station 16. Alternatively, coupling can be accomplished by inserting the token key 132 into the body electronics unit 14, removing the token key 132 from the body electronics unit, inserting the token key 132 into the base station 16, removing the token key 132 from the base station 16 and reinserting the token key 132 into the body electronics unit 14. In step 206, electrical signals from the patient's heart are detected and transmitted to the body electronics unit 14 via chest assembly 12 and the precordial assembly 60. In step 208, the electrical signals from the heart are transformed by the body electronics unit 14 from analog signals to digital signals. In step 210, the body electronics unit 14 transmits the digital signals to the base station 16 via radio transmission. In step 212, the base station 16 transforms the digital signals into analog signals. In step 214, the base station 16 transmits the analog signals to the ECG monitor 138 via monitor cables 174. In step 216, the ECG monitor 138 processes the analog signals into meaningful information that can be displayed on the monitor 138.

In the foregoing specification, the present invention has been described with reference to specific exemplary embodiments thereof. It will be apparent to those skilled in the art, that a person understanding this invention may conceive of changes or other embodiments or variations, which utilize the principles of this invention without departing from the broader spirit and scope of the invention. The specification and drawings are, therefore, to be regarded in an illustrative rather than restrictive sense. Accordingly, it is not intended that the invention be limited except as may be necessary in view of the appended claims.

We claim:

1. A system for converting a conventional, non-wireless electrocardiograph monitoring system to a wireless electrocardiograph monitoring system comprising:
a body electronics unit for acquiring electrical signals from a chest or precordial assembly and wirelessly transmitting the electrical signals to a base station, the base station a having a plurality of terminals for directly transmitting the electrical signals to any conventional electrocardiograph monitor, the base station having a user interface for communicating information to the user and further comprising an apparatus for pairing the base station with the body electronics unit wherein the apparatus is a removable token key being physically separable from said body electronics unit and said base station.

2. The system of claim 1 wherein the base station controls the data collected by the chest assembly.

3. The system of claim 1 wherein the chest assembly has five electrode connectors for connecting to electrodes.

4. The system of claim 3 wherein an electrode is positioned on the right side of a patient's chest about level of the first and second intercostal space, an electrode is positioned on the left side of the patient's chest about level of the first and second intercostals space, an electrode is positioned in the middle of the patient's chest about level of the fourth and fifth intercostals space, and two electrodes are positioned on the left side of the patient's torso.

5. The system of claim 1 wherein the on body electronics unit and the base station each have a battery port for removably retaining a battery.

6. The system of claim 5 wherein the battery is compatible with the battery port of the body electronics unit and the battery port of the base station.

7. A method of pairing the body electronics unit of claim 1 with the base station by:
inserting the token key into a token key port of the base station to record an identification number of the base station;
removing the token key from the token key port of the base station;
inserting the token key into the token key port of the body electronics unit to record an identification number of the body electronics unit and to transmit the identification number of the base station to the body electronics unit;
removing the token key port from the token key port of the body electronics unit;
and inserting the token key into the token key port of the base station to transfer the identification number of the body electronics unit to the base station.

8. A method of pairing the body electronics unit of claim 1 with the base station by
inserting the token key into the token key port of the body electronics unit to record an identification number or the body electronics unit;
removing the token key from the token key port of the body electronics unit;
inserting the token key into a token key port of the base station to record an identification number of the base station and to transmit the identification number of the body electronics unit to the base station;
removing the token key port from the token key port of the base station; and
inserting the token key into the token key port of the body electronics to transfer the identification number of the base station to the body electronics unit.

9. A system for monitoring cardiac activity in a patient comprising, in combination:
an assembly having a plurality of electrode connectors removably connected to a plurality electrodes that detect electrical signals from a patient's heart;
a body electronics unit removably connected to the assembly, the body electronics unit acquiring the electrical signals from the assembly and transmitting the electrical signals to a base station via radio transmission, the body electronics unit having a user interface for communicating information to the user;
the base station including a receiver for receiving the electrical signals and a plurality of terminals for directly connecting to an electrocardiograph monitor via monitor cables, the base station having a user interface for communicating information to the user and further comprising a removable token key for pairing the body electronics unit with the base station, said token key being physically separable from said body electronics unit and said base station.

10. The system of claim 9 wherein the user interfaces of the body electronics unit and the base station communicate information pertaining to the system's operating status.

11. The system of claim 9 wherein the base station includes a cradle for storing the body electronics unit.

12. A system for monitoring cardiac activity in a patient comprising, in combination:
a chest assembly having a plurality of electrode connectors removably connected to a plurality of electrodes that detects electrical signals from a patient's heart;
a precordial assembly having a plurality of electrode connectors removably connected to a plurality of electrodes that detect electrical signals from a patient's heart;
a body electronics unit removably connected to the chest assembly connector and the precordial assembly connector, the body electronics unit receiving the electrical signals from the chest assembly and the precordial assembly;
a base station for acquiring the electrical signals from the body electronics unit via radio frequency transmission, the base station having a plurality of terminals the connecting to electrocardiograph monitor cables, the electrical signals transmitted to an electrocardiograph monitor via the electrocardiograph monitor cables further comprising a removable token key for pairing the body electronics unit with the base station wherein said token key is physically separable from said body electronics unit and said base station.

13. The system of claim 12 wherein the body electronics unit includes a user interface for communicating information to the user.

14. The system of claim 12 wherein the base station includes a user interface for communicating information to the user.

15. The system of claim 12 wherein the base station includes a cradle for storing the body electronics unit.

16. A system for wireless transmission of physiological signals from a physiological sensor to a monitor comprising:
a body electronics unit, the physiological sensor removably coupled to the body electronics unit, the physiological signals transmitted to the body electronics unit whereby the body electronics unit wirelessly transmits the physiological signals to a base station, the base station a having a plurality of terminals for directly transmitting the physiological signals to any conventional monitor, the base station having a user interface for communicating information to the user and further comprising a token key for pairing the body electronics unit with the base station, said removable token key physically separable from said body electronics unit and said base station.

17. The system of claim 16 wherein the physiological signals pertain to information selected from the group consisting of pulse, respiration rate, heart rate, temperature, EEG signals, and pulse oximeter signals.

18. A base station for use in a system for monitoring cardiac activity in a patient comprising:
a receiver for receiving electrical signals sent from a body electronics unit; and
a plurality of terminals for directly connecting to conventional electrocardiograph monitor cables for transmitting the electrical signals to a conventional electrocardiograph monitor and a removable token key for pairing the body electronics unit to the base station.

19. The base station of claim 18 further comprising a user interface for communicating information to a user.

20. The base station of claim 19 wherein the information pertains to the system's operating status.

21. The base station of claim 18 further comprising a battery port for removably receiving a base station battery.

22. The base station of claim 21 wherein the base station battery is interchangeable with a body electronics unit battery.

23. The base station of claim 18 further comprising a lead switch for instructing the base station to operate in either a 7 lead mode or 12 lead mode.

24. The base station of claim 18 wherein the base station is removably secured to an ECG monitor.

25. A method of monitoring the cardiac activity in a patient comprising the steps of:
positioning a chest assembly on a patient's body, the chest assembly having a plurality of electrode connectors for connecting to a plurality of electrodes;
plugging the chest assembly into a body electronics unit, the body electronics unit having a user interface that communicates information to a user and wherein the body electronics unit is activated by plugging the chest assembly into the body electronics unit;
pairing the body electronics unit with a base station through the use of a removable token key;
detecting electrical signals from the patient's heart with the chest assembly;
transmitting the electrical signals from the chest assembly to the body electronics unit;
transforming the electrical signals from analog signals into digital signals;
transmitting the digital signals to the base station via radio transmission, the base station having a user interface for communicating information to the user and a plurality of terminals for transmitting the electrical signals to an electrocardiograph monitor;
transforming the digital signals into analog signals; and
transmitting the analog signals directly to the electrocardiograph monitor via the terminals.

* * * * *

UNITED STATES PATENT AND TRADEMARK OFFICE
CERTIFICATE OF CORRECTION

PATENT NO. : 7,197,357 B2
APPLICATION NO. : 09/998733
DATED : March 27, 2007
INVENTOR(S) : Istvan et al.

It is certified that error appears in the above-identified patent and that said Letters Patent is hereby corrected as shown below:

On the title page (73), delete "Life Sync" and insert therefor --LifeSync--.

Signed and Sealed this

Twenty-second Day of May, 2007

JON W. DUDAS
*Director of the United States Patent and Trademark Office*